United States Patent
Masel et al.

(10) Patent No.: US 9,957,624 B2
(45) Date of Patent: May 1, 2018

(54) ELECTROCHEMICAL DEVICES COMPRISING NOVEL CATALYST MIXTURES

(71) Applicant: Dioxide Materials, Inc., Boca Raton, FL (US)

(72) Inventors: Richard I. Masel, Boca Raton, FL (US); Zengcai Liu, Boca Raton, FL (US); Brian Rosen, Wilmington, DE (US)

(73) Assignee: Dioxide Materials, Inc., Boca Raton, FL (US)

( * ) Notice: Subject to any disclaimer, the term of this patent is extended or adjusted under 35 U.S.C. 154(b) by 0 days. days.

(21) Appl. No.: 15/226,894

(22) Filed: Aug. 2, 2016

(65) Prior Publication Data

US 2017/0022618 A1 Jan. 26, 2017

Related U.S. Application Data

(63) Continuation-in-part of application No. 14/591,902, filed on Jan. 7, 2015, now Pat. No. 9,464,359, which
(Continued)

(51) Int. Cl.
*C25B 3/04* (2006.01)
*B01J 41/14* (2006.01)
(Continued)

(52) U.S. Cl.
CPC ........... *C25B 11/0405* (2013.01); *B01J 31/02* (2013.01); *C01B 32/40* (2017.08); *C07C 45/00* (2013.01);
(Continued)

(58) Field of Classification Search
USPC ................................................. 429/483, 479
See application file for complete search history.

(56) References Cited

U.S. PATENT DOCUMENTS

| 1,919,850 A | 7/1933 | Luscher |
| 2,511,198 A | 6/1950 | Engel |

(Continued)

FOREIGN PATENT DOCUMENTS

| CA | 1272180 A | 7/1990 |
| CA | 2821642 A | 6/2012 |

(Continued)

OTHER PUBLICATIONS

Li et al., "Novel anion exchange membranes based on polymerizable imidazolium salt for alkaline fuel cell applications", J. Mater. Chem. 21 (2011), pp. 11340-11346.*

(Continued)

*Primary Examiner* — Mark Kaucher
*Assistant Examiner* — Henry Hu
(74) *Attorney, Agent, or Firm* — Corridor Law Group, P.C.

(57) ABSTRACT

Electrochemical devices comprising electrocatalyst mixtures include at least one Catalytically Active Element and, as a separate constituent, one Helper Catalyst. The electrocatalysts can be used to increase the rate, modify the selectivity or lower the overpotential of chemical reactions. These electrocatalysts are useful for a variety of chemical reactions including, in particular, the electrochemical conversion of $CO_2$. Chemical processes employing these catalysts produce CO, $HCO^-$, $H_2CO$, $(HCOO)^-$, HCOOH, $CH_3OH$, $CH_4$, $C_2H_4$, $CH_3CH_2OH$, $CH_3COO^-$, $CH_3COOH$, $C_2H_6$, $(COOH)_2$, or $(COO^-)_2$. Devices using the electrocatalysts include, for example, a $CO_2$ sensor and a $CO_2$ electrolyzer.

16 Claims, 18 Drawing Sheets

Related U.S. Application Data is a continuation of application No. 13/626,873, filed on Sep. 25, 2012, now Pat. No. 8,956,990, which is a continuation of application No. PCT/US2011/030098, filed on Mar. 25, 2011, which is a continuation of application No. 12/830,338, filed on Jul. 4, 2010, now abandoned, application No. 15/226,894, which is a continuation-in-part of application No. 15/090,477, filed on Apr. 4, 2016, now Pat. No. 9,580,824, which is a continuation-in-part of application No. 14/704,935, filed on May 5, 2015, now Pat. No. 9,370,773, which is a continuation-in-part of application No. PCT/US2015/026507, filed on Apr. 17, 2015, which is a continuation of application No. PCT/US2015/014328, filed on Feb. 3, 2015.

(60) Provisional application No. 61/317,955, filed on Mar. 26, 2010, provisional application No. 62/066,823, filed on Oct. 21, 2014.

(51) Int. Cl.
| | | |
|---|---|---|
| C25B 11/04 | (2006.01) | |
| C25B 9/08 | (2006.01) | |
| C25B 1/00 | (2006.01) | |
| B01J 31/02 | (2006.01) | |
| C07C 45/00 | (2006.01) | |
| C25B 3/00 | (2006.01) | |
| H01M 8/0612 | (2016.01) | |
| H01M 4/90 | (2006.01) | |
| C01B 32/40 | (2017.01) | |
| G01N 27/48 | (2006.01) | |
| H01M 8/00 | (2016.01) | |
| G01N 27/416 | (2006.01) | |

(52) U.S. Cl.
CPC .......... *C25B 1/00* (2013.01); *C25B 3/00* (2013.01); *C25B 3/04* (2013.01); *C25B 9/08* (2013.01); *C25B 11/04* (2013.01); *C25B 11/0415* (2013.01); *C25B 11/0447* (2013.01); *H01M 4/90* (2013.01); *H01M 8/0612* (2013.01); *G01N 27/416* (2013.01); *G01N 27/48* (2013.01); *H01M 8/00* (2013.01); *Y02P 20/135* (2015.11)

(56) References Cited

U.S. PATENT DOCUMENTS

| | | |
|---|---|---|
| 2,996,359 A | 8/1961 | Mossman et al. |
| 3,959,094 A | 5/1976 | Steinberg |
| 4,207,151 A | 6/1980 | Franke et al. |
| 4,240,882 A | 12/1980 | Ang et al. |
| 4,315,526 A | 2/1982 | Bruckenstein et al. |
| 4,474,652 A | 10/1984 | Brown et al. |
| 4,523,981 A | 6/1985 | Ang et al. |
| 4,545,872 A | 10/1985 | Sammells et al. |
| 4,595,465 A | 6/1986 | Ang et al. |
| 4,608,132 A | 8/1986 | Sammells |
| 4,608,133 A | 8/1986 | Morduchowitz et al. |
| 4,609,440 A | 9/1986 | Frese et al. |
| 4,609,441 A | 9/1986 | Frese et al. |
| 4,620,906 A | 11/1986 | Ang |
| 4,668,349 A | 5/1987 | Cuellar et al. |
| 4,673,473 A | 6/1987 | Ang et al. |
| 4,756,807 A | 7/1988 | Meyer et al. |
| 4,771,708 A | 9/1988 | Douglass |
| 4,789,442 A | 12/1988 | Nakagawa et al. |
| 4,818,353 A | 4/1989 | Langer et al. |
| 4,879,070 A | 11/1989 | Kent |
| 4,968,393 A | 11/1990 | Mazur et al. |
| 5,064,733 A | 11/1991 | Krist et al. |
| 5,071,526 A | 12/1991 | Pletcher et al. |
| 5,089,661 A | 2/1992 | Maspero et al. |
| 5,206,433 A | 4/1993 | Hohenschutz et al. |
| 5,284,563 A | 2/1994 | Fujihira et al. |
| 5,294,740 A | 3/1994 | Kiefer et al. |
| 5,334,759 A | 8/1994 | Lippert et al. |
| 5,362,367 A | 11/1994 | Dapperheld et al. |
| 5,382,332 A | 1/1995 | Fujihira et al. |
| 5,639,910 A | 6/1997 | Ikariya et al. |
| 5,709,789 A | 1/1998 | Shay et al. |
| 5,763,622 A | 6/1998 | Podszun et al. |
| 5,804,045 A | 9/1998 | Orillon et al. |
| 5,879,915 A | 3/1999 | Loubiere et al. |
| 5,928,806 A | 7/1999 | Olah et al. |
| 5,952,540 A | 9/1999 | Kyu et al. |
| 6,024,855 A | 2/2000 | Sharifian et al. |
| 6,099,990 A | 8/2000 | Denton et al. |
| 6,429,333 B1 | 8/2002 | Saari et al. |
| 6,660,680 B1 | 12/2003 | Hampden-Smith et al. |
| 6,706,657 B2 | 3/2004 | Commereuc et al. |
| 6,713,649 B1 | 3/2004 | Hladiy et al. |
| 6,841,700 B2 | 1/2005 | Auer et al. |
| 6,849,764 B2 | 2/2005 | Gurkaynak et al. |
| 6,867,329 B2 | 3/2005 | Auer et al. |
| 6,906,222 B2 | 6/2005 | Slany et al. |
| 6,955,743 B2 | 10/2005 | Rousu et al. |
| 6,987,134 B1 | 1/2006 | Gagnon |
| 6,992,212 B2 | 1/2006 | Zehner et al. |
| 7,081,547 B2 | 7/2006 | Fujimoto et al. |
| 7,157,404 B1 | 1/2007 | Jun et al. |
| 7,241,365 B2 | 7/2007 | Auer et al. |
| 7,253,316 B2 | 8/2007 | Pastre et al. |
| 7,323,593 B2 | 1/2008 | Adami et al. |
| 7,351,860 B2 | 4/2008 | Adami et al. |
| 7,420,088 B2 | 9/2008 | Karl et al. |
| 7,459,590 B2 | 12/2008 | Olah et al. |
| 7,479,570 B2 | 1/2009 | Ogo et al. |
| 7,605,293 B2 | 10/2009 | Olah et al. |
| 7,608,743 B2 | 10/2009 | Olah et al. |
| 7,612,233 B2 | 11/2009 | Hauk et al. |
| 7,618,725 B2 | 11/2009 | Masel et al. |
| 7,704,369 B2 | 4/2010 | Olah et al. |
| 8,313,634 B2 | 11/2012 | Bocarsly et al. |
| 8,592,633 B2 | 11/2013 | Cole et al. |
| 8,956,990 B2 * | 2/2015 | Masel ............ B01J 19/08 |
| | | 429/416 |
| 9,464,359 B2 * | 10/2016 | Masel ............ B01J 19/08 |
| 2004/0031685 A1 | 2/2004 | Anderson et al. |
| 2006/0096871 A1 | 5/2006 | Manoukian et al. |
| 2006/0234174 A1 | 10/2006 | Burrahm et al. |
| 2006/0235091 A1 | 10/2006 | Olah et al. |
| 2007/0036706 A1 | 2/2007 | Ogo et al. |
| 2007/0045125 A1 | 3/2007 | Hartvigsen et al. |
| 2007/0187247 A1 | 8/2007 | Lackner et al. |
| 2008/0039538 A1 | 2/2008 | Olah et al. |
| 2008/0103040 A1 | 5/2008 | Rodriguez et al. |
| 2008/0223727 A1 | 9/2008 | Oloman |
| 2009/0014336 A1 | 1/2009 | Olah et al. |
| 2009/0016948 A1 | 1/2009 | Young |
| 2009/0169452 A1 | 7/2009 | Constantz et al. |
| 2009/0289211 A1 | 11/2009 | Fujioka et al. |
| 2010/0132556 A1 | 6/2010 | Constantz et al. |
| 2010/0133120 A1 | 6/2010 | Varney et al. |
| 2010/0135865 A1 | 6/2010 | Constantz et al. |
| 2010/0137457 A1 | 6/2010 | Kaplan |
| 2010/0187123 A1 | 7/2010 | Bocarsly et al. |
| 2010/0193370 A1 | 8/2010 | Olah et al. |
| 2010/0276287 A1 | 11/2010 | Manoukian et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0226632 A1 | 9/2011 | Cole et al. |
| 2011/0237830 A1 * | 9/2011 | Masel ............ B01J 31/0278 |
| | | 562/550 |

(56) References Cited

U.S. PATENT DOCUMENTS

| | | | | |
|---|---|---|---|---|
| 2013/0105304 | A1* | 5/2013 | Kaczur | C25B 9/10 204/237 |
| 2014/0378561 | A1 | 12/2014 | Van Berchum et al. | |

FOREIGN PATENT DOCUMENTS

| | | |
|---|---|---|
| CN | 101250711 | 11/2010 |
| DE | 183856 A | 1/1906 |
| EP | 0012215 B1 | 6/1980 |
| EP | 0293230 A2 | 11/1988 |
| EP | 0323300 A1 | 7/1989 |
| GB | 2230782 A | 10/1990 |
| JP | S58-110684 | 7/1983 |
| JP | H04-013883 | 5/1990 |
| JP | H0-017554 A | 1/1998 |
| JP | 2004-533545 | 11/2004 |
| JP | 2007-515283 | 6/2007 |
| JP | H20-517749 A | 5/2008 |
| JP | 2009-511740 | 3/2009 |
| JP | H24-201217300 A | 1/2012 |
| WO | 2008110830 A1 | 9/2008 |
| WO | 2010007602 A1 | 1/2010 |
| WO | 2010063626 A1 | 6/2010 |
| WO | 2011120021 A1 | 9/2011 |
| WO | 2012006240 A1 | 1/2012 |
| WO | 2013006711 A1 | 1/2013 |

OTHER PUBLICATIONS

Lin et al., "Alkaline Stable C2-Substituted Imidazolium-Based Anion-Exchange Membranes", Chem. Mater. 25 (2013), pp. 1858-1867.*
Zhang et al., "Imidazolium functionalized polysulfone anion exchange membrane for fuel cell application", J. Mater. Chem. 21 (2011), pp. 12744-12752.*
Rosen al., "Ionic Liquid-Mediated Selective Conversion of CO2 to CO at Low Overpotentials", Science 334 (2011), pp. 643-644.
Solla-Gullon et al., "Shape dependent electrocatalysis", Annual Reports on the Progress of Chemistry—Section C 107 (2011), pp. 263-297.
International Search Report dated Jul. 6, 2011, in connection with PCT/2011/030098.
International Search Report and Written Opinion of the International Searching Authority dated Oct. 31, 2011, in connection with PCT/US2011/042809.
Written Opinion of the International Searching Authority dated Sep. 26, 2012, in connection with PCT/US2011/030098.
Chen et al., "Role of surface defect sites: From Pt model surfaces to shape-controlled nanoparticles", Chem. Science 3 (2012), pp. 136-147.
Singh et al., "Comparison of Oxygen Reduction Reaction at Silver Nanoparticles and Polycrystalline Silver Electrodes in Alkaline Solution", J. Phys. Chem. 116 (2012), pp. 10656-10663.
Yu et al., "Carboxylation of Terminal Alkynes with Carbon Dioxide Catalyzed by Poly(N-Heterocyclic Carbene)—Supported Silver Nanoparticles", Adv. Synth. Catal. 354 (2012), pp. 969-974.
International Preliminary Report on Patentability dated Jan. 3, 2013 in connection with International Application No. PCT/US2011/030098.
International Preliminary Report on Patentability dated Jan. 3, 2013 in connection with International Application No. PCT/US2011/042809.
International Search Report and Written Opinion dated Feb. 15, 2013 in connection with PCT/US2012/043651.
Deng et al., "Linked strategy for the production of fuels via formose reaction", Scientific Reports 3 (2013), p. 1244.
Third-Party Submissions Under 37 CFR 1.290, submitted on Sep. 17 and 18, 2013, in connection with co-owned U.S. Appl. No. 12/830,338, and Concise Description of Relevance for each of the references cited in the Third Party Submissions.
Zhu et al., "Monolayers of choline chloride can enhance desired electrochemical reactions and inhibit undesirable ones", Electrochimica Acta 96 (2013), pp. 18-22.
International Preliminary Report on Patentability dated Jan. 9, 2014 in connection with International Application PCT/US2012/043651.
International Search Report and Written Opinion dated May 16, 2014 in connection with PCT/US2013/061506.
International Search Report and Written Opinion dated Jun. 17, 2014 in connection with PCT/US2014/018067.
Chinese Office Action dated Aug. 5, 2014 in connection with Chinese Application No. 201180023851.2.
Patent Examination Report No. I dated Dec. 12, 2014 in connection with Australian Application 2011230545.
Office Action dated Jan. 27, 2015 in connection with Japanese Application 2013-501536.
Chinese Office Action dated Oct. 16, 2015 in connection with Chinese Application No. 201180033161.5.
Korean Office Action dated Aug. 1, 2016 in connection with Korean Patent Application No. 10-2012-7027866.
Kaneco et al., "Carbon dioxide sequestration technology by electrochemical conversion at cadmium electrode in methanol under mild conditions", Photo/ & Photobiology in Environment, Energy and Fuel (2003), pp. 181-189.
Liu et al., "General rules for predicting where a catalytic reaction should occur on metal surfaces: A density functional theory study of C-H and C-0 bond breaking/making on flat, stepped, and kinked metal surfaces", J. of the American Chem. Soc. 125 (2003), pp. 1958-1967.
Magdesieva et al., "Lutetium monophthalocyanine and diphthalocyanine complexes and lithium naphthalocyanine as catalysts for electrochemical CO2 reduction", J. of the Electrochem. Soc. 150 (2003), pp. E608-E612.
Aulice et al., "Electrochemical Reduction of Carbon Dioxide: A Status Report", Indian Natn. Sci. Acad., vol. 70, A No. 3 (2004), pp. 407-462.
Jessop et al., "Recent advances in the homogeneous hydrogenation of carbon dioxide", Coordination Chem. Rev. 248 (2004), pp. 2425-2442.
Koleli et al., "Reduction of CO2 under high pressure and high temperature on Pb-granule electrodes in a fixed-bed reactor in aqueous medium", Applied Catalysis A-General 274 (2004), pp. 237-242.
Maillard et al., "Size effects on reactivity of Pt nanoparticles in Co mono layer oxidation: The role of surface mobility", Faraday Discussions 125 (2004), pp. 357-377.
Ogura et al., "Selective formation of ethylene from CO2 by catalytic electrolysis at a three-phase interface", Prepr. Pap.—Am. Chem. Soc., Div. Fuel Chem. 49 (2004), pp. 9-10.
Ramirez et al., "A supramolecular cobalt-porphyrin-modified electrode, toward the electroreduction of CO2", J. of Coordination Chemistry 57 (2004), pp. 249-255.
Star et al., "Nanoelectric carbon dioxide sensors", Advanced Materials 16 (2004), pp. 2049-2051.
Yano et al., "Selective electrochemical reduction of CO2 to ethylene at a three-phase interface on copper(I) halide-confined Cumesh electrodes in acidic solutions of potassium halides", J. of Electroanalytical Chemistry 565 (2004), pp. 287-293.
Zhao et al., "Electrochemical reduction of supercritical carbon dioxide in ionic liquid 1-n-butyl-3-methylimidazolium 1-hexafluorophosphate", J. of Supercritical Fluids 32 (2004), pp. 287-291.
Arenz et al., "The effect of the particle size on the kinetics of CO electrooxidation on high surface area Pt catalysts", J. of the American Chem. Soc. 127 (2005), pp. 6819-6829.
Dube et al., "Influence of adsorption processes on the CO2 electroreduction: an electrochemical mass spectrometry study", J. of Electroanalytical Chemistry 582 (2005), pp. 230-240.
Isaacs et al., "Electrochemical reduction of CO2 mediated by poly-M-aminophthalocyanines (M=Co, Ni, Fe): poly-Co-tetraaminophthalocyanine, a selective catalyst", Journal of Molecular Catalysis A: Chemical 229 (2005), pp. 249-257.

(56) References Cited

OTHER PUBLICATIONS

Laitar et al., "Efficient homogeneous catalysis in the reduction of CO2 to Co", J. of the American Chem. Soc. 127 (2005), pp. 17196-17197.
Maillard et al., "Influence of particle agglomeration on the catalytic activity of carbon-supported Pt nanoparticles in Co mono layer oxidation", Physical Chemistry Chem. Physics 7 (2005), pp. 385-393.
Narayanan et al., "Catalysis with transition metal nanoparticles in colloidal solution: Nanoparticle shape dependence and stability", J. of Physical Chemistry B 109 (2005), pp. 12663-12676.
Ogura et al., "Reduction of CO2 to ethylene at three-phase interface effects of electrode substrate and catalytic coatin", J. of the Electrochem. Soc. 152 (2005), pp. D213-D219.
Perez et al., "In situ FT-IR and ex situ EPR analysis for the study of the electroreduction of carbon dioxide in N, Ndimethylformamide on a gold interface", J. of Electroanalytical Chemistry 578 (2005), pp. 87-94.
Qu et al., "Electrochemical reduction of CO2 on Ru0i/Ti02 nanotubes composite modified Pt electrode", Electrochimica Acta 50 (2005), pp. 3576-3580.
Rodriguez et al., "Specific surface reactions for identification of platinum surface domains: Surface characterization and electrocatalytic tests", Electrochimica Acta 50 (2005), pp. 4308-4317.
Smolinka et al., " CO2 reduction on Pt electrocatalysts and its impact on H 2 oxidation in CO2 containing fuel cell feed gas—A combined in situ infrared spectroscopy, mass spectrometry and fuel cell performance study", Electrochimica Acta 50 (2005), pp. 5189-5199.
Blizanac et al., "Oxygen Reduction on Silver Low-Index Single-Crystal in Alkaline Solution: Rotating Ring DiskAg (hk1)", J. Phys. Chem. 110 (2006), pp. 4735-4741.
Dubois. in A. Bard, ed., "Encyclopedia of Electrochem.", 7a, Springer (2006), pp. 202-225.
Gattrell et al. "A review of the aqueous electrochemical reduction of CO2 to hydrocarbons at copper", J. of Electroanalytical Chem. 594 (2006), pp. 1-19.
Kaneco et al., "Electrochemical reduction of carbon dioxide to ethylene at a copper electrode in methanol using potassium hydroxide and rubidium hydroxide supporting electrolytes", Electrochimica Ada 51 (2006), pp. 3316-3321.
Kaneco et al., "Electrochemical reduction of CO2 in copper particle-suspended methanol", Chem. Engineering J. 119 (2006), pp. 107-112.
Kaneco et al., "Electrochemical reduction of CO2 to Methane at the Cu electrode in methanol with sodium supporting salts and its comparison with other alkaline salts", Energy & Fuels 20 (2006), pp. 409-414.
Li et al. "Development of a continuous reactor for the electroreduction of carbon dioxide to formate—Part 1: Process variables", J. of Applied Electrochem. 36 (2006), pp. 1105-1115.
Raebiger et al., "Electrochemical Reduction of CO2 to Co Catalyzed by a Bimetallic Palladium Complex", Organometallics 25 (2006), pp. 3345-3351.
Silvester et al., "Electrochemistry in room temperature ionic liquids: A review and some possible applications", Z. Phys. Chem. 220 (2006), pp. 1247-1274.
Solla-Gullon et al., "Co monolayer oxidation on semi-spherical and preferentially oriented (100) and (111) platinum nanoparticles", Electrochem. Communications 8 (2006), pp. 189-194.
Yano et al., "Particle-size effect of nanoscale platinum catalysts in oxygen reduction reaction: An electrochemical and 195Pt EC-NMR study", Physical Chemistry Chem. Physics 8, (2006), pp. 4932-4939.
Yano et al., "Selective ethylene formation by pulse-mode electrochemical reduction of carbon dioxide using copper and copperoxide electrodes", J. of Solid State Electrochem. 11 (2006), pp. 554-557.

Zhou et al., "Size effects in electronic and catalytic properties of unsupported palladium nanoparticles in electrooxidation of formic acid", J. of Physical Chem. B 110 (2006), pp. 13393-13398.
Dubois, "Electrochemical Reactions of Carbon Dioxide", Encyclopedia of Electrochem. (2007), p. 212.
Begum et al., "Electrocatalysis of CO2 reduction by ruthenium benzothiazole and bithiazole complexes", Electrochem. Communications 9 (2007), pp. 2525-2528.
Gattrell et al., "Electrochemical reduction of CO2 to hydrocarbons to store renewable electrical energy and upgrade biogas", Energy Conversion Management 48 (2007), pp. 1255-1265.
Himeda, "Conversion of CO2 into formate by homogeneously catalyzed hydrogenation in water: tuning catalytic activity and water solubility through the acid-base equilibrium of the ligand", European J. of Inorganic Chemistry (2007), pp. 3927-3941.
Jitaru, "Electrochemical carbon dioxide reduction—Fundamental applied topics (Review)", J. of the Univ. of Chem. Tech. and Metallurgy 42 (2007), pp. 333-344.
Kaneco et al. "Effect of sodium cation on the electrochemical reduction of CO2 at a copper electrode in methanol", J. of Solid State Electrochem. 11 (2007), pp. 490-495.
Lee et al., "Studies on suppression of hydrogen evolution reaction for zinc/air fuel cell", Material Science Forums 539-543 (2007), pp. 1427-1430.
Li et al., "Development of a continuous reactor for the electro-reduction of carbon dioxide to formate—Part 2: Scale-up", J. of Applied Electrochem. 37 (2007), pp. 1107-1117.
Lukaszewski et al., "Comparative EQCM study on electrooxidation of carbon oxides adsorption products on noble metals and their alloys. Polycrystalline Pd-based systems", J. of Electroanalytical Chemistry 606 (2007), pp. 117-133.
Subramanian et al., "Electrochemical membrane reactor for the reduction of carbon dioxide to formate", J. of Applied Electrochem. 37 (2007), pp. 255-260.
Tian et al., "Synthesis of tetrahexahedral platinum nanocrystals with high-index facets and high electro-oxidation activity", Science 316 (2007), pp. 732-735.
Xu et al., "Effects of imidazolium salts as cocatalysts on the copolymerization of CO2 with epoxides catalyzed by (salen)CrmCI complex", Polymer 48 (2007), pp. 3921-3924.
Yoshizawa-Fujita et al., "A new class of proton-conducting ionic plastic crystals based on organic cations and dihydrogen phosphate", Electrochem. Communications 9 (2007), pp. 1202-1205.
Zhu, "Supported cholinechloride/urea as a heterogeneous catalyst for chemical fixation of carbon dioxide to cyclic carbonates", Green Chem. vol. 9 (2007), pp. 169-172.
Pease et al., "The catalytic combination of ethylene and hydrogen in the presence of metallic copper. III. Carbon monoxide as a catalyst poison", J. Am. Chem. Soc. 47 (1925), pp. 1235-1240.
Urey et al., "Some reactions of atomic hydrogen", J. of the American Chem. Soc. 51 (1929), pp. 3286-3290.
Udupa et al., "Electrolytic reduction of carbon dioxide to formic acid", Electrochimica Acta 16 (1971), pp. 1593-1598.
Bregoli, "The influence of platinum crystallite size on the electrochemical reduction of oxygen in phosphoric acid", Electrochimica Acta 23 (1978), pp. 489-492.
Fisher et al., "Electrocatalytic reduction of carbon dioxide by using macrocycles of nickel and cobalt", J. Am. Chem. Soc., vol. 102, No. 24 (1980), pp. 7361-7363.
Weiss et al., "Formose sugars from formaldehyde", Applied Catalysis 1 (1981), pp. 237-246.
Eggins et al., "Voltammetry of carbon dioxide. Part 1. A general survey of voltammetry at different electrode materials in different solvents", J. Electroanalytical Chem. 148 (1983), pp. 17-24.
Danly, "Development and commercialization of the Monsanto electrochemical adiponitrile process", J. Electrochem. Soc. 131 (1984), pp. 435C-442C.
Franklin et al., "The effect of quaternary ammonium salts on the anodic oxidation of ethanol", Surface Technology 24 (1985), pp. 143-155.

(56) References Cited

OTHER PUBLICATIONS

Chandrasekaran et al., "In-situ spectroscopic investigation of adsorbed intermediate radicals in electrochemical reactions: carbon dioxide CO2 on platinum", Surface Science 185 (1987), pp. 495-514.
Ikeda et al., "Selective Formation of Formic Acid. Oxalic Add, and Carbon Monoxide by Electrochemical Reduction of Carbon Dioxide", Bull. Chem. Soc. Japan, vol. 60 (1987), pp. 2517-2522.
Dewulf et al., "The electrochemical reduction of CO2 to CH4 and C2H4 at Cu/Nation electrodes (solid polymer electrolyte structures)", Catalysis Letters 1 (1988), pp. 73-80.
Dewulf et al., "Electrochemical and surface studies of carbon dioxide reduction to methane and ethylene at copper electrodes in aqueous solutions", J. of the Electrochem. Soc. 136 (1989), pp. 1686-1691.
Azuma et al., "Electrochemical reduction of carbon dioxide on various metal, electrodes in low-temperature aqueous KHCO3 media", J. Electrochem. Soc. 137 (1990), pp. 1772-1778.
Hori et al., "Electrochemical evidence of intermediate formation of adsorbed carbon monoxide in cathodic reduction of carbon dioxide ata nickel electrode", Electrochimica Acta 35 (1990), pp. 1777-1780.
Kinoshita, "Particle size effects for oxygen reduction on highly dispersed platinum in acid electrolytes", J. of the Electrochem. Soc. 137 (1990), pp. 845-848.
Noda et al., "Electrochemical reduction of carbon dioxide at various metal electrodes in aqueous potassium hydrogen aarbonate solution", Bull. Chem. Soc. Japan 63 (1990), pp. 2459-2462.
Dubois et al., "Electrochemical reduction of carbon dioxide catalyzed by [Pd(triphosphine)(solvent)](BF4)2 complexes: synthetic and mechanistic studies", J. Am. Chem. Soc., vol. 113. No. 23 (1991), pp. 8753-8764.
Derien et al., "Activation of carbon dioxide: nickel-catalyzed electrochemical carboxylation of diynes", J. Organic Chem. vol. 58. No. 9 (1993), pp. 2578-2588.
Kabbabi et al., "Particle size effect for oxygen reduction and methanol oxidation on Pt/C inside a proton exchange membrane", J. of Electroanalytical Chemistry 373 (1994), pp. 251-254.
Meiwes-Broer, "Work functions of metal clusters", Hyperfine Interactions 89 (1994), pp. 263-269.
Podlovchenko et al., "Electroreduction of carbon dioxide on palladium electrodes at potentials higher than the reversible hydrogen potential", J. of Electroanalytical Chemistry 373 (1994), pp. 185-187.
Saeki et al., "Electrochemical reduction of liquid CO2 Drastic enhancement of current density", J. of the Electrochem. Soc. 141 (1994), pp. L130-L132.
Seshadri et al., "A new homogeneous electrocatalyst for the reduction of carbon dioxide to methanol at low overpotential", J. Electroanalytical Chemistry 372 (1994), pp. 145-150.
Dietz et al., "Influence of substituted benzaldehydes and their derivatives as inhibitors for hydrogen evolution in lead/acid batteries", J. of Power Sources 53 (1995), pp. 359-365.
Idriss et al., "Two routes to formaldehyde from formic acid on TiO2, (001) surfaces", Surface Science 348 (1996), pp. 39-48.
Saeki et al., "Electrochemical reduction of CO2 with high current density in a CO2 + methanol medium at various metal electrodes", J. of Electroanalytical Chemistry 404 (1996), pp. 299-302.
Eggins et al., "Improved yields of oxalate, glyoxylate and glycolate from the electrochemical reduction of carbon dioxide in methanol", J. of Applied Electrochem. 27 (1997), pp. 706-712.
Furuya et al., "High performance Ru-Pd catalysts for CO2 reduction at gas-diffusion electrodes", J. of Electroanalytical Chemistry 431 (1997), pp. 39-41.
Hoshi et al., "Electrochemical reduction of CO2 on single crystal electrodes of Ag(111), Ag(100), and Ag(110)", J. of Electroanalytical Chemistry 440 (1997), pp. 283-286.
Popic et al., "Reduction of carbon dioxide on ruthenium oxide and modified ruthenium oxide electrodes in 0.5 M NaHCO3", J. of Electroanalytical Chem. 421 (1997), pp. 105-110.
Sung et al., "Structure of chemisorbed sulfur on a Pt(III) electrode", J. of the American Chem. Soc. 119 (1997), pp. 194-200.
Kaneco et al., "Electrochemical conversion of carbon dioxide to formic acid on Pb in KOH/methane electrolyte at ambient temperature and pressure", Energy, vol. 23, No. 12 (1998), pp. 1107-1112.
Smolinski et al., "Effect of surface order on adsorption of sulfate ions on silver electrodes", J. of Electroanalytical Chemistry 442 (1998), pp. 41-47.
Sobkowski et al., "Interaction of sulfate ions with monocrystalline silver electrodes", Colloids Surfaces A: Physicochern. Eng. Aspects 134 (1998), pp. 39-45.
Yano et al., "Effects of additives in zinc alloy powder on suppressing hydrogen evolution", J. of Power Sources 74 (1998), pp. 129-134.
Ikeda et al., "Zinc ion effect on electrochemical reduction of carbon dioxide at zinc electrode in aqueous solutions", Electrochem. (Tokyo) 67 (1999), pp. 27-33.
Kaneco et al., "Electrochemical reduction of carbon dioxide to ethylene with high Faradaic efficiency at a Cu electrode in CsOH/methanol", Electrochimica Acta 44 (1999), pp. 4701-4706.
Welton, "Room-Temperature Ionic Liquids. Solvents for Synthesis and Catalysis". Chem. Revs., vol. 99, No. 8 (1999), pp. 2071-2083.
Hoshi et al., "Electrochemical reduction of carbon dioxide at a series of platinum single crystal electrodes", Electrochimica Acta 45 (2000), pp. 4263-4270.
Kiss et al., "Palladium-catalyzed reppe carbonylation", Chem. Rev. 101 (2001), pp. 3435-3456.
Masel, "Chemical Kinetics and Catalysis", Wiley (2001), pp. 702-742.
Ishida et al., "High-Temperature Electrochemical Reduction of Carbon Dioxide Using an Ionic Liquid", The Chem. Soc. of Jpn, Proceeding of 82th Autumn Meeting, Sep. 10, (2002), pp. 46, IA6-01.
Takahashi et al., "Electrochemical reduction of CO2 at copper single crystal Cu(S)-[n(111) A-(111)] and Cu(S)-[n (110) A- (100)] electrodes", J. of Electroanalytical Chemistry 533 (2002), pp. 135-143.
Yang et al., "Electrochemical activation of carbon dioxide in ionic liquid: synthesis of cyclic carbonates at mild reaction conditions", Chem. Commun. (2002), pp. 274-275.
Chaplin et al., "Effects of process conditions and electrode material on reaction pathways for carbon dioxide electroreduction with particular reference to formate formation", J. of Applied Electrochem. 33 (2003), pp. 1107-1123.
Cherstiouk et al., "Model approach to evaluate particle size effects in electrocatalysis: Preparation and properties of Pt nanoparticles supported on GC and HOPG", Electrochimica Acta 48 (2003), pp. 3851-3860.
Davis et al., "Commercially available salts as building blocks for new ionic liquids", ACS Symp. Ser. 856 (2003), pp. 100-107.
Hori et al., "Electrochemical reduction of carbon dioxide at various series of copper single crystal electrodes", J. of Molecular Catalysis A: Chem. 199 (2003), pp. 39-47.
Hoshi et al., "Electrochemical reduction of carbon dioxide on kinked stepped surfaces of platinum inside the stereographic triangle", J. of Electroanalytical Chemistry 540 (2003), pp. 105-110.
Bell, "Basic Research Needs: Catalysis for Energy", U.S. Department of Energy Report PNNL-17214 (2008), p. 69.
Chu et al., "Fixation of CO2 by electrocatalytic reduction and electropolymerization in ionic liquid-H20 solution", Chem. Sus. Chem. 1 (2008), pp. 205-209.
Delacourt et al., "Design of an electrochemical cell making syngas 18 (CO+ H2-) from CO2 and H20 reduction at room temperature", J. of the Electrochem. Soc. 155 (2008), pp. B42-B49.
Delacourt et al., "Mathematical modeling of a cation-exchange membrane containing two cations", J. of the Electrochem. Soc. 155 (2008), pp. B1210-B1217.
Fukuzumi, "Bioinspired Energy Conversion Systems for Hydrogen Production and Storage", Eur. J. Inorg. Chem., vol. 2008. No. 9. (2008),pp. 1351-1362.
Hori, "Electrochemical CO2 reduction on metal electrodes", Modem Aspects of Electrochem. 42 (2008), pp. 89-189.

(56) References Cited

OTHER PUBLICATIONS

Ikeda et al., "Electrochemical reduction of carbon dioxide using gas diffusion electrodes loaded with fine catalysts", Nanoscience and Nanotechnology (2008), pp. 108-113.
Jiang et al., "Solvent-free synthesis of substituted ureas from CO2 and amines with a functional ionic liquid as the catalyst", Green Chem. 10 (2008), pp. 465-469.
Kinge et al., "Dependence of CO oxidation on Pt nanoparticle shape: a shape-selective approach to the synthesis of PEMFC catalysts", Applied Organometallic Chemistry 22 (2008), pp. 49-54.
Li et al., "Absorption of CO2 by ionic liquid/polyethylene glycol mixture and the thermodynamic parameters", Royal Society of Chemistry Green Chem. 10 (2008), pp. 879-884.
Oloman et al., "Electrochemical processing of carbon dioxide", Chem. Sus. Chem. 1 (2008), pp. 385-391.
O'Mahony et al., "The electrochemical reduction of hydrogen sulfide on platinum in several room temperature ionic liquids", The J. of Physical Chemistry CI 12 (2008), pp. 7725-7730.
Rezaei et al., "Effects of tetrabutylammonium hydrogen sulfate as an electrolyte additive on the electrochemical behavior of lead acid battery", J. of Solid State Electrochem. 12 (2008), pp. 1663-1671.
Scheijen et al., "The electrooxidation of small organic molecules on platinum nanoparticles supported on gold: Influence of platinum deposition procedure", J. of Solid State Electrochem. 12 (2008), pp. 483-495.
Silvester et al., "Electrochemical reduction of benzoic acid and substituted benzoic acids in some room temperature ionic liquids", The J. of Physical Chemistry C 112 (2008), pp. 12966-12973.
Solla-Gullon et al., "Shape-dependent electrocatalysis: Methanol and formic acid electrooxidation on preferentially oriented Pt nanoparticles", Physical Chemistry Chem. Physics 10 (2008), pp. 3689-3698.
Sun et al., "Hydroxyl-functionalized ionic liquid: a novel efficient catalyst for chemical fixation of CO2 to cyclic carbonate", Tetrahedron Letters 49 (2008), pp. 3588-3591.
Tian et al., "Platinum metal catalysts of high-index surfaces: from single-crystal planes to electrochemically shape-controlled nanoparticles", J. of Physical Chemistry C 112 (2008), pp. 19801-19817.
Wong et al., "A robust ionic liquid as reaction medium and efficient organocatalyst for carbon dioxide fixation", Chem. Sus. Chem. 1 (2008), pp. 67-70.
Yang et al., "Electrodeposition of Tin and Antimony in Ethyl-3-Methylimidazolium Tetrafluoroborate Ionic Liquid", J. Appl. Electrochem 38 (2008), 537-542.
Zhang et al., "Electrochemical activation of CO2 in ionic liquid (BMIMBF4 ): synthesis of organic carbonates under mild conditions", Green Chemistry 10 (2008), pp. 202-206.
Zhang et al., "Hydrogenation of carbon dioxide is promoted by a task-specific ionic liquid", Angew. Chem. Int. Ed. 47 (2008), pp. 1127-1129.
Barrosse-Antle et al., "Reduction of carbon dioxide in 1-butyl-3-methylimidazolium acetate", Chem. Commun. (2009), pp. 3744-3746.
Cheung et al., "Electrocatalytic reduction of carbon dioxide by a polymeric film of rhenium tricarbonyl dipyridylamine", J. of Organometallic Chemistry 694 (2009), pp. 2842-2845.
Haerens et al., "Electrochemical decomposition of choline chloride based ionic liquid analogues", Green Chemistry 11 (2009), pp. 1357-1365.
Ikeda et al., "Electrochemical Reduction of Carbon Dioxide Using Gas Diffusion Electrodes Loaded With Fine Catalysts", Nanoscience and Nanotechnology 1136 (2009), pp. 108-113.
Innocent et al., "Electro-reduction of carbon dioxide to formate on lead electrode in aqueous medium", J. of Applied Electrochem. 39 (2009), pp. 227-232.
Kaneco et al., "Photoelectrochemical reduction of CO2 at p-InP electrode in copper particle-suspended methanol", Chem. Engineering J. 148 (2009), pp. 57-62.

Liu et al., "Observation of surface structural changes of Pt octahedron nanoparticles and its effect in electrocatalysis oxidation of methanol", Catalysis Communications 10 (2009), pp. 1244-1247.
Lukaszewski et al., "Electrosorption of carbon dioxide on platinum group metals and alloys-a review", J. of Solid State Electrochem. 13 (2009), pp. 813-827.
Ma et al., "A short review of catalysis for CO2 conversion", Catal. Today 148 (2009), pp. 221-231.
Ohya et al., "Electrochemical reduction of CO2 in methanol with aid of CuO and Cu2O", Catalysis Today 148 (2009), pp. 329-334.
Photinon et al., "Thick-Film carbon dioxide sensor via anodic adsorbate stripping technique and its structural dependence", Sensors 9 (2009), pp. 7203-7216.
Rakowski et al., "Development of molecular electrocatalysts for CO2 reduction and H2 production/oxidation", Acc. Chem. Res. 42 (2009), pp. 1974-1982.
Rezaei et al., "Application of ionic liquids as an electrolyte additive on the electrochemical behavior of lead acid battery", J. of Power Sources 187 (2009), pp. 605-612.
Yan et al., "Adsorption of CO2 on the rutile (110) surface in ionic liquid. A molecular dynamics simulation", J. Phys. Chem. C 113 (2009), pp. 19389-19392.
Yuan et al., "Electrochemical activation of carbon dioxide for synthesis of dimethyl carbonate in an ionic liquid", Electrochimica Acta 54 (2009), pp. 2912-2915.
Zhang et al., "Chiral ionic liquids improved the asymmetric cycloaddition of CO2 to epoxides", Green Chem. 11 (2009), pp. 935-938.
Zhang et al., "Hydrogenation of CO2 to formic acid promoted by a diamine-functionalized ionic liquid", Chem. Sus. Chem. 2 (2009), pp. 234-238.
Cahill et al., "Investigation of proton dynamics and the proton transport pathway in choline dihydrogen phosphate using solid state NMR", Physical Chemistry Chemical Physics 12 (2010), pp. 5431-5438.
Cole et al., "Using a one-electron shuttle for the multielectron reduction of CO2 to methanol: kinetic, mechanism, and structural insights", J. Am. Chem. Soc. 132 (2010), pp. 11539-11551.
Li., "Electrocatalytic Reduction of CO2 to Small Organic Molecule Fuels on Metal Catalysts", Advances In CO2 Conversion and Utilization (2010), pp. 55-76.
Lopez-Cudero et al., "CO electrooxidation on carbon supported platinum nanoparticles: Effect of aggregation", J. of Electroanalytical Chemistry 644 (2010), pp. 117-126.
Ogura et al., "CO2 attraction by specifically adsorbed anions and subsequent accelerated electrochemical reduction", Electrochimica Acta 56 (2010), pp. 381-386.
Tian et al., "Direct electrodeposition of tetrahexahedral Pd nanocrystals with high-index facets and high catalytic activity for ethanol electrooxidation", J. of the American Chem. Soc. 132 (2010), pp. 7580-7581.
Gazsi et al., "Decomposition and reforming of formic acid on supported Au catalysts: Production of CO-free H2", J. of Physical Chem. C 115 (2011), pp. 15459-15466.
Sabatier et al., "Chimie Organique.—Sur la decomposition catalytique de I 'acide formique", Comptes Rendus lebdomadaires Des Seances De L'Academie Dessciences 152 (2011), pp. 1213-1215.
Koper, "Structure sensitivity and nanoscale effects in electrocatalysis", Nanoscale 3 (2011), pp. 2054-2073.
Morris et al., "Electrocatalytic carbon dioxide activation: The rate-determining step of pyridinium-catalyzed CO2 reduction", Chem. Sus. Chem, 4 (2011), pp. 191-196.
Perez et al., "Particle size effect for ethanol electro-oxidation on Pt/C catalysts in half-cell and in a single direct ethanol fuel cell", J. of Electroanalytical Chemistry 654 (2011), pp. 108-115.
Yang et al., "Electrodeposition of Tin and Antimony in 1-Ethyl-3-Methylimidazolium Tetrafluoroborate Ionic Liquid", J. Appl. Electrochem vol. 38, No. 4, Dec. 25, 2007, pp. 537-542.
Office Action issued by the Japanese Patent Office dated Dec. 20, 2016, in connection with Japanese Patent Application No. 2015-232576.

(56) References Cited

OTHER PUBLICATIONS

Non-Final Office Action dated Mar. 29, 2017, in connection with U.S. Appl. No. 14/592,246.
Office Action issued by the European Patent Office dated Mar. 31, 2017, in connection with European Patent Application No. 11713569.9.
Office Action issued by the Canadian Intellectual Property Office (CIPO) dated Jun. 8, 2017, in connection with Canadian Patent Application No. 2,794,105.

* cited by examiner

ELECTROCHEMICAL DEVICES COMPRISING NOVEL CATALYST MIXTURES

CROSS-REFERENCE TO RELATED APPLICATIONS

This application is a continuation-in-part of U.S. patent application Ser. No. 14/591,902 filed on Jan. 7, 2015 now U.S. Pat. No. 9,464,359 issued on Nov. 11, 2016. The '902 application was a continuation of U.S. patent application Ser. No. 13/626,873 filed on Sep. 25, 2012 (now U.S. Pat. No. 8,956,990 issued on Feb. 17, 2015). The '873 application was a continuation of International application No. PCT/US2011/030098, having an international filing date of Mar. 25, 2011, entitled "Novel Catalyst Mixtures". The '098 international application claimed priority benefits, in turn, from U.S. provisional patent application Ser. No. 61/317,955 filed on Mar. 26, 2010, and continuation status from U.S. non-provisional patent application Ser. No. 12/830,338 filed on Jul. 4, 2010. Each of the '902 patent application, the '873 application, the '098 international application, the '955 provisional application, and the '338 non-provisional application is hereby incorporated by reference herein in its entirety.

This application is also a continuation-in-part of U.S. patent application Ser. No. 15/158,227 filed on May 18, 2016. The '227 application is a continuation-in-part, in turn, of U.S. patent application Ser. No. 15/090,477 filed on Apr. 4, 2016. The '477 application is a continuation-in-part, in turn, of U.S. patent application Ser. No. 14/704,935 filed on May 5, 2015 (now U.S. Pat. No. 9,370,773 issued on Jun. 21, 2016). The '935 application was a continuation-in-part of International application No. PCT/US2015/26507, having an international filing date of Apr. 17, 2015, which was a continuation of International application No. PCT/US2015/14328 filed on Feb. 3, 2015. The '328 application claimed priority benefits from U.S. provisional patent application Ser. No. 62/066,823 filed on Oct. 21, 2014. The '507 international application also claimed priority benefits from the '823 provisional application. Each of the '227 application, the '477 application, the '935 application, the '507 international application, the '328 international application, and the '823 provisional application is hereby incorporated by reference herein in its entirety.

STATEMENT OF GOVERNMENT INTEREST

This invention was made, at least in part, with U.S. government support under ARPA-E Contract No. DE-AR-0000345. The government has certain rights in the invention.

FIELD OF THE INVENTION

The field of the invention is electrochemical devices comprising electrocatalysts. The electrochemical devices and electrocatalysts of this invention are applicable, for example, to the electrochemical conversion of carbon dioxide into useful products.

BACKGROUND OF THE INVENTION

There is a present need to decrease carbon dioxide ($CO_2$) emissions from industrial facilities. Over the years, a number of electrochemical processes have been suggested for the conversion of $CO_2$ into useful products. Processes for $CO_2$ conversion and the catalysts for them are discussed in U.S. Pat. Nos. 3,959,094, 4,240,882, 4,523,981, 4,545,872, 4,595,465, 4,608,132, 4,608,133, 4,609,440, 4,609,441, 4,609,451, 4,620,906, 4,668,349, 4,673,473, 4,711,708, 4,756,807, 4,818,353, 5,064,733, 5,284,563, 5,382,332, 5,457,079, 5,709,789, 5,928,806, 5,952,540, 6,024,855, 6,660,680, 6,987,134 (the '134 patent), U.S. Pat. Nos. 7,157,404, 7,378,561, 7,479,570, U.S. Pat. App. Pub. No. 2008/0223727 (the '727 application) and papers reviewed by Hori (Modern Aspects of Electrochemistry, 42, 89-189, 2008) ("the Hori Review"), Gattrell, et al. (Journal of Electroanalytical Chemistry, 594, 1-19, 2006) ("the Gattrell review"), DuBois (Encyclopedia of Electrochemistry, 7a, 202-225, 2006) ("the DuBois review"), and the papers Li, et al. (Journal of Applied Electrochemistry, 36, 1 105-1115, 2006, Li, et al. (Journal of Applied Electrochemistry, 37, 1107-1 117, 2007, and Oloman, et al. (ChemSusChem, 1, 385-391, 2008) ("the Li and Oloman papers").

Generally, an electrochemical cell contains an anode 50, a cathode 51 and an electrolyte 53, as indicated in FIG. 1. The cell can also include a membrane 52. Catalysts are placed on the anode, and or cathode and or in the electrolyte to promote desired chemical reactions. During operation, reactants or a solution containing reactants is fed into the cell. Then a voltage is applied between the anode and the cathode, to promote an electrochemical reaction.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds. Examples of cathode reactions in the Hori Review include:

$$CO_2 + 2e^- \rightarrow CO + O^{2-}$$

$$2CO_2 + 2e^- \rightarrow CO + CO_3^{2-}$$

$$CO_2 + H_2O + 2e^- \rightarrow CO + 2OH^-$$

$$CO_2 + 2H_2O + 4e^- \rightarrow HCO^- + 3OH^-$$

$$CO_2 + 2H_2O + 2e^- \rightarrow H_2CO + 2OH^-$$

$$CO_2 + H_2O + 2e^- \rightarrow (HCO_2)^- + OH^-$$

$$CO_2 + 2H_2O + 2e^- \rightarrow H_2CO_2 + 2OH-$$

$$CO_2 + 6H_2O + 6e^- \rightarrow CH_3OH + 6OH^-$$

$$CO_2 + 6H_2O + 8e^- \rightarrow CH_4 + 8OH^-$$

$$2CO_2 + 8H_2O + 12e^- \rightarrow C_2H_4 + 12OH^-$$

$$2CO_2 + 9H_2O + 12e^- \rightarrow CH_3CH_2OH + 12OH^-$$

$$2CO_2 + 6H_2O + 8e^- \rightarrow CH_3COOH + 8OH^-$$

$$2CO_2 + 5H_2O + 8e^- \rightarrow CH_3COO^- + 7OH^-$$

$$CO_2 + 10H_2O + 14e^- \rightarrow C_2H_6 + 14OH^-$$

$$CO_2 + 2H^+ + 2e^- \rightarrow CO + H_2O, \text{ acetic acid, oxalic acid, oxylate}$$

$$CO_2 + 4H^+ + 4e^- \rightarrow CH_4 + O_2$$

where e- is an electron. The examples given above are merely illustrative and are not meant to be an exhaustive list of all possible cathode reactions.

Examples of reactions on the anode mentioned in the Hori Review include:

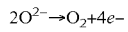
$2O^{2-} \rightarrow O_2 + 4e-$

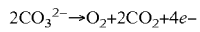
$2CO_3^{2-} \rightarrow O_2 + 2CO_2 + 4e-$

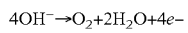
$4OH^- \rightarrow O_2 + 2H_2O + 4e-$

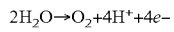
$2H_2O \rightarrow O_2 + 4H^+ + 4e-$

The examples given above are merely illustrative and are not meant to be an exhaustive list of all possible anode reactions.

In the previous literature, catalysts comprising one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sin, Tb, La, Ce, and Nd have all shown activity for $CO_2$ conversion. Reviews include Ma, et al. (Catalysis Today, 148, 221-231, 2009), Hori (Modern Aspects of Electrochemistry, 42, 89-189, 2008), Gattrell, et al. (Journal of Electroanalytical Chemistry, 594, 1-19, 2006), DuBois (Encyclopedia of Electrochemistry, 7a, 202-225, 2006) and references therein.

The results in the Hori Review show that the conversion of $CO_2$ is only mildly affected by solvent unless the solvent also acts as a reactant. Water can act like a reactant, so reactions in water are different than reactions in non-aqueous solutions. But the reactions are the same in most non-aqueous solvents, and importantly, the overpotentials are almost the same in water and in the non-aqueous solvents.

Zhang, et al. (ChemSusChem, 2, 234-238, 2009) and Chu, et al. (ChemSusChem, 1, 205-209, 2008) report $CO_2$ conversion catalyzed by an ionic liquid. Zhao, et al. (The Journal of Supercritical Fluids, 32, 287-291, 2004) and Yuan, et al., (Electrochimica Acta 54 (2009) 2912-2915) report the use of an ionic liquid as a solvent and electrolyte, but not a co-catalyst, for $CO_2$ electroconversion. Each of these papers is incorporated by reference. Catalyst Today Volume 48, pages 189-410 November 2009 provides the proceedings of the 10th international conference on $CO_2$ utilization. These pages are incorporated by reference. The catalysts have been in the form of either bulk materials, supported particles, collections of particles, small metal ions or organometallics. Still, according to Bell (A. Bell. Ed, Basic Research Needs, Catalysis For Energy, U.S. Department Of Energy Report PNNL17712, 2008) ("the Bell Report"), "The major obstacle preventing efficient conversion of carbon dioxide into energy-bearing products is the lack of catalyst" with sufficient activity at low overpotentials and high electron conversion efficiencies.

The overpotential is associated with lost energy of the process, and so one needs the overpotential to be as low as possible. Yet, according to The Bell Report "Electron conversion efficiencies of greater than 50 percent can be obtained, but at the expense of very high overpotentials". This limitation needs to be overcome before practical processes can be obtained.

The '134 patent also considers the use of salt (NaCl) as a secondary "catalyst" for $CO_2$ reduction in the gas phase, but salt does not lower the overpotential for the reaction.

A second disadvantage of many of the catalysts is that they also have low electron conversion efficiency. Electron conversion efficiencies over 50% are needed for practical catalyst systems.

The examples above consider applications for $CO_2$ conversion, but the invention overcomes limitations of other systems. For example, some commercial $CO_2$ sensors use an electrochemical reaction to detect the presence of $CO_2$. At present, these sensors require over 1-5 watts of power, which is too high for portable sensing applications.

Finally, the invention considers new methods to form formic acid. Other methods are discussed in U.S. Pat. Nos. 7,618,725, 7,612,233, 7,420,088, 7,351,860, 7,323,593, 7,253,316, 7,241,365, 7,138,545, 6,992,212, 6,963,909, 6,955,743, 6,906,222, 6,867,329, 6,849,764, 6,841,700, 6,713,649, 6,429,333, 5,879,915, 5,869,739, 5,763,662, 5,639,910, 5,334,759, 5,206,433, 4,879,070, and 4,299,891. These processes do not use $CO_2$ as a reactant.

SUMMARY OF THE INVENTION

The invention provides a novel catalyst mixture that can overcome one or more of the limitations of low rates, high overpotentials and low electron conversion efficiencies (namely, selectivities) for catalytic reactions and high power for sensors. The catalyst mixture includes at least one Catalytically Active Element, and at least one Helper catalyst. When the Catalytically Active Element and the Helper Catalyst are combined, the rate and/or selectivity of a chemical reaction can be enhanced over the rate seen in the absence of the Helper Catalyst. For example, the overpotential for electrochemical conversion of carbon dioxide can be substantially reduced, and the current efficiency (namely, selectivity) for $CO_2$ conversion can be substantially increased.

The invention specifically includes Helper Catalysts in the form of Positively Charged Cyclic Amines. The Positively Charged Cyclic Amines. This specifically includes imidazoliums, pyridiniums, pyrazoliums, pyrrolidiniums, pyrroliums, pyrimidiums, piperidiniums, indoliums, triaziniums, and polymers thereof.

The invention is not limited to catalysts for $CO_2$ conversion. In particular, catalysts that include Catalytically Active Elements and Helper Catalysts might enhance the rate of a wide variety of chemical reactions. Reaction types include: homogeneously catalyzed reactions, heterogeneously catalyzed reactions, chemical reactions in chemical plants, chemical reactions in power plants, chemical reactions in pollution control equipment and devices, chemical reactions in fuel cells, and chemical reactions in sensors. The invention includes all of these examples. The invention also includes processes using these catalysts.

DETAILED DESCRIPTION OF ILLUSTRATIVE EMBODIMENT(S)

Figure 1:
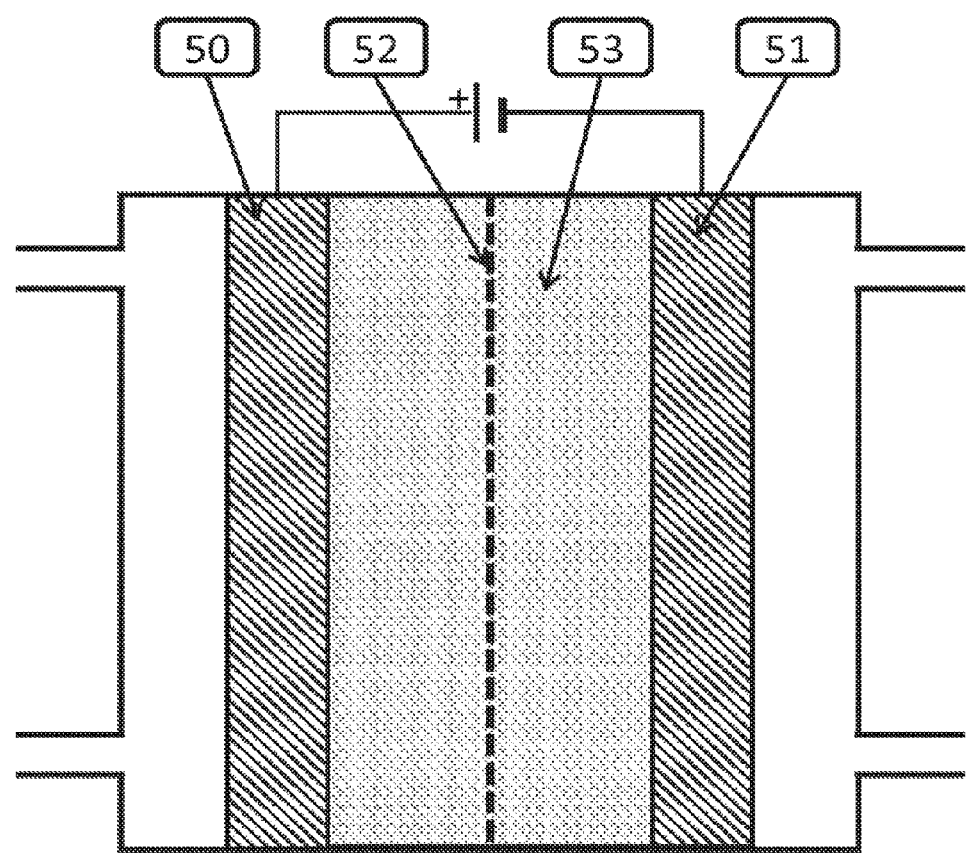
FIG. 1 is a diagram of a typical electrochemical cell.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical value ranges recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

Definitions

The term "electrochemical conversion of $CO_2$" as used here refers to any electrochemical process where carbon dioxide, carbonate, or bicarbonate is converted into another chemical substance in any step of the process.

The term "CV" as used here refers to a cyclic voltammogram or cyclic voltammetry.

The term "Overpotential" as used here refers to the potential (voltage) difference between a reaction's thermodynamically determined reduction or oxidation potential and the potential at which the event is experimentally observed.

The term "Cathode Overpotential" as used here refers to the overpotential on the cathode of an electrochemical cell.

The term "Anode Overpotential" as used here refers to the overpotential on the anode of an electrochemical cell.

The term "Electron Conversion Efficiency" refers to selectivity of an electrochemical reaction. More precisely, it is defined as the fraction of the current that is supplied to the cell that goes to the production of a desired product.

The term "Catalytically Active Element" as used here refers to any chemical element that can serve as a catalyst for the electrochemical conversion of $CO_2$.

The term "Helper Catalyst" refers to any organic molecule or mixture of organic molecules that does at least one of the following:
(a) Speeds up a chemical reaction, or
(b) Lowers the overpotential of the reaction without being substantially consumed in the process.

The term "Active Element, Helper Catalyst Mixture" refers to any mixture that includes one or more Catalytically Active Element(s) and at least one Helper Catalyst.

The term "Ionic Liquid" refers to salts or ionic compounds that form stable liquids at temperatures below 200° C.

The term "Deep Eutectic Solvent" refers to an ionic solvent that includes a mixture which forms a eutectic with a melting point lower than that of the individual components.

The term "imidazolium" as used here refers to a positively charged ligand containing an imidazole group. This includes a bare imidazole or a substituted imidazole. Ligands of the form:

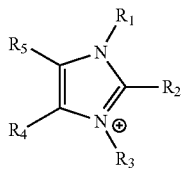

where $R_1$-$R_5$ are each independently selected from hydrogen, halides linear alkyls, branched alkyls, cyclic alkyls, heteroalkyls, aryls, heteroaryls, alkylaryls, heteroalkylaryls, and polymers thereof, such as the vinyl benzyl copolymers described herein, are specifically included.

The term "pyridinium" as used here refers to a positively charged ligand containing a pyridine group. This includes a bare pyridine or a substituted pyridine.

Ligands of the Form

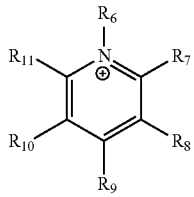

where $R_6$-$R_{11}$ are each independently selected from hydrogen, halides, linear alkyls, branched alkyls, cyclic alkyls, heteroalkyls, aryls, heteroaryls, alkylaryls, heteroalkylaryls, and polymers thereof are specifically included.

The term "phosphonium" as used here refers to a positively charged ligand containing phosphorous. This includes substituted phosphorous. Ligands of the form:

$P+(R_{12}R_{13}R_{14}R_{15})$ where $R_{12}$-$R_{15}$ are each independently selected from hydrogen, halides, linear alkyls, branched alkyls, cyclic alkyls, heteroalkyls, aryls, heteroaryls, alkylaryls, heteroalkylaryls, and polymers thereof are specifically included.

The term "Positively Charged Cyclic Amine" as used here refers to a positively charged ligand containing a cyclic amine. This specifically includes imidazoliums, pyridiniums, pyrazoliums, pyrrolidiniums, pyrroliums, pyrimidiums, piperidiniums, indoliums, triaziniums, and polymers thereof such as the vinyl benzyl copolymers described herein, are specifically included.

Specific Description

The invention relates generally to Active Element, Helper Catalyst Mixtures where the mixture does at least one of the following:

Speeds up a chemical reaction, or

Lowers the overpotential of the reaction, without being substantially consumed in the process.

For example, such mixtures can lower the overpotential for $CO_2$ conversion to a value less than the overpotentials seen when the same Catalytically Active Element is used without the Helper Catalyst.

According to the Hori Review, Gattrell, et al. (Journal of Electroanalytical Chemistry, 594, 1-19, 2006), DuBois (Encyclopedia of Electrochemistry, 7a, 202-225, 2006) and references therein, catalysts including one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sin, Tb, La, Ce, and Nd all show activity for $CO_2$ conversion. Products include one or more of CO, OH$^-$, HCO$^-$, $H_2CO$, $(HCO_2)^-$, $H_2O_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$. Therefore, V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sin, Tb, La, Ce, and Nd are each examples of Catalytically Active Elements, but the invention is not limited to this list of chemical elements. Possible products of the reaction include one or more of CO, OH$^-$, HCO$^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$, but the invention is not limited to this list of products.

The Hori Review also notes that Pb, Hg, Tl, In, Cd, Bi, Zr, Cr, Sn and W are best for formic acid production. Furuya, et al. (Journal of Electroanalytical Chemistry, 431, 39-41, 1997) notes that Pd/Ru is also active.

The Hori Review notes that there has been over 30 years of work on the electrochemical conversion of $CO_2$ into saleable products, but still, according to the Bell Report "Electron conversion efficiencies of greater than 50 percent can be obtained, but at the expense of very high overpotentials". This limitation needs to be overcome before practical processes can be obtained.

Figure 2:
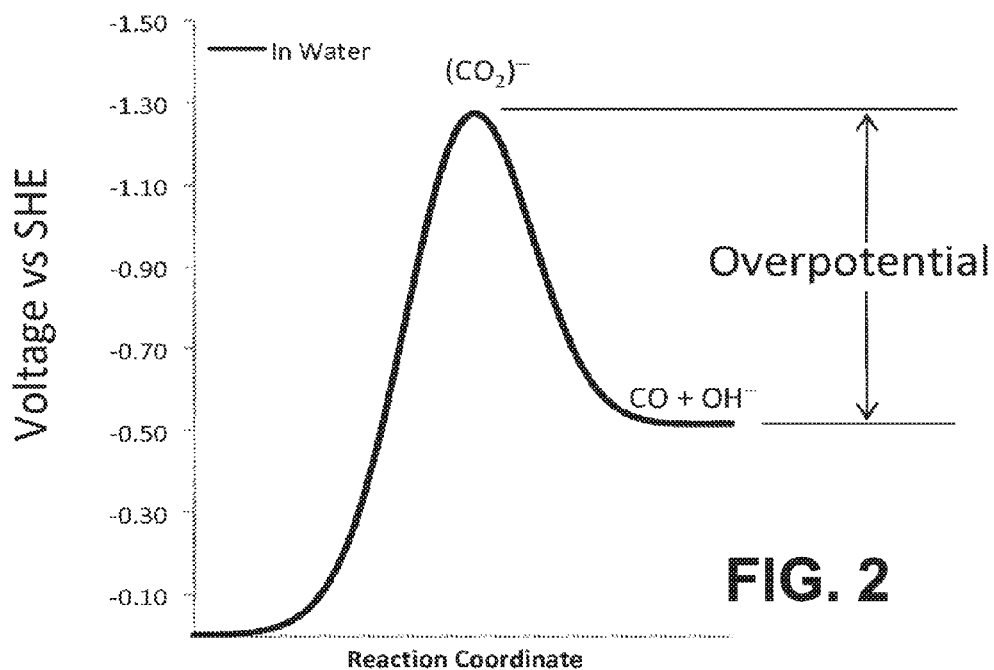
FIG. 2 is a schematic of how the potential of the system moves as it proceeds along the reaction coordinate in the absence of the ionic liquid if the system goes through a $(CO_2)^-$ intermediate. The reaction coordinate indicates the fraction of the reaction that has been completed. A high potential for $(CO_2)^-$ formation can create a high overpotential for the reaction.
Figure 3:
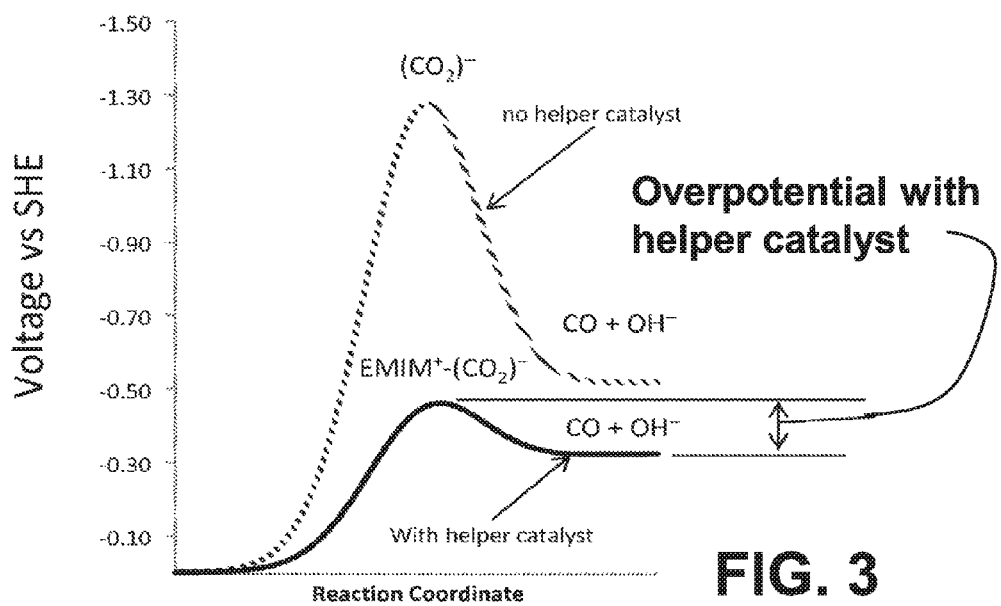
FIG. 3 illustrates how the potential could change when a Helper Catalyst is used. In this case the reaction could go through a $CO_2$-EMIM complex rather than a $(CO_2)^-$, substantially lowering the overpotential for the reaction.
Figure 4A:
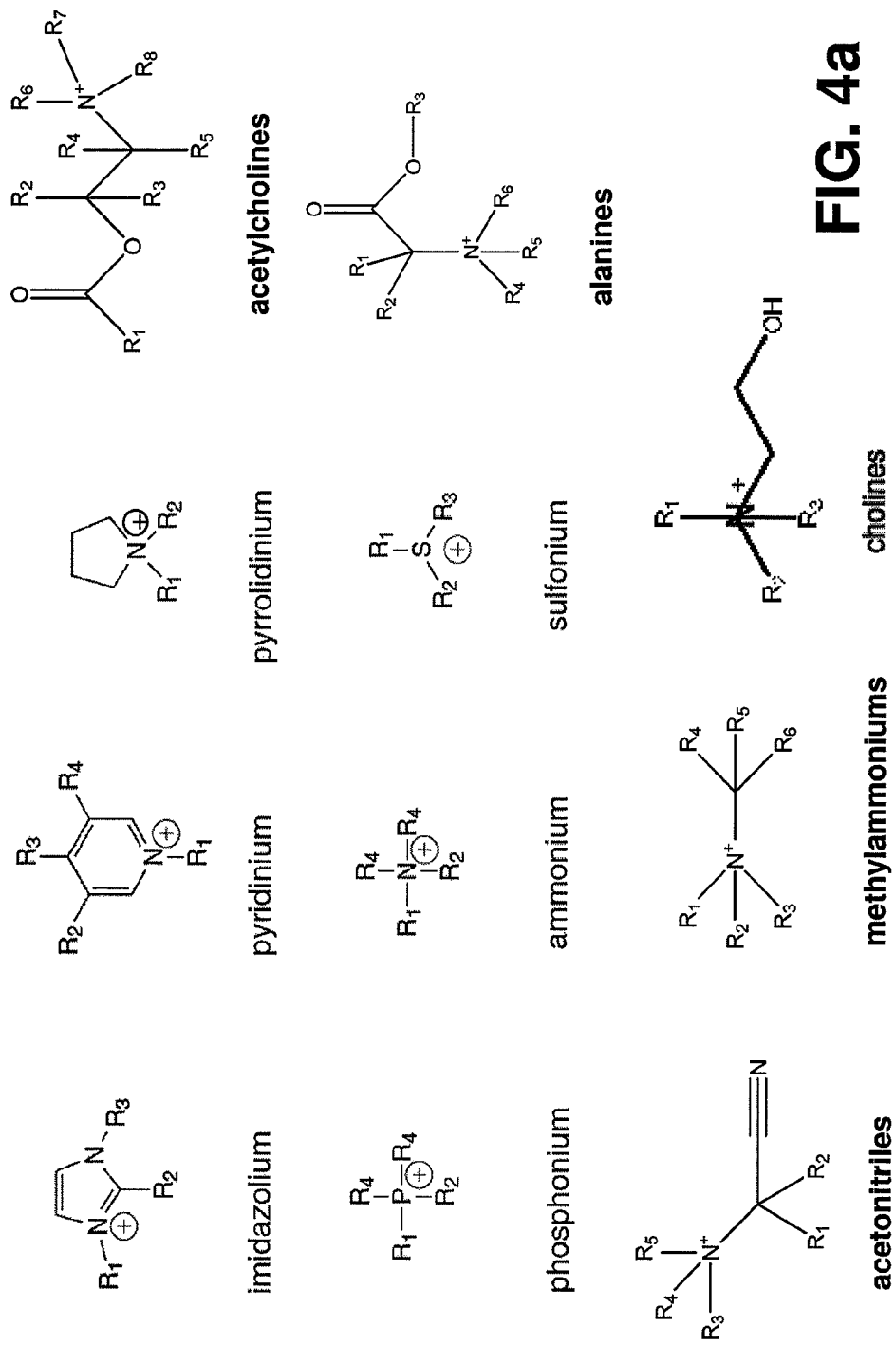
FIGS. 4a, 4b and 4c illustrate some of the cations that may be used to form a complex with $(CO_2)^-$.
Figure 4B:
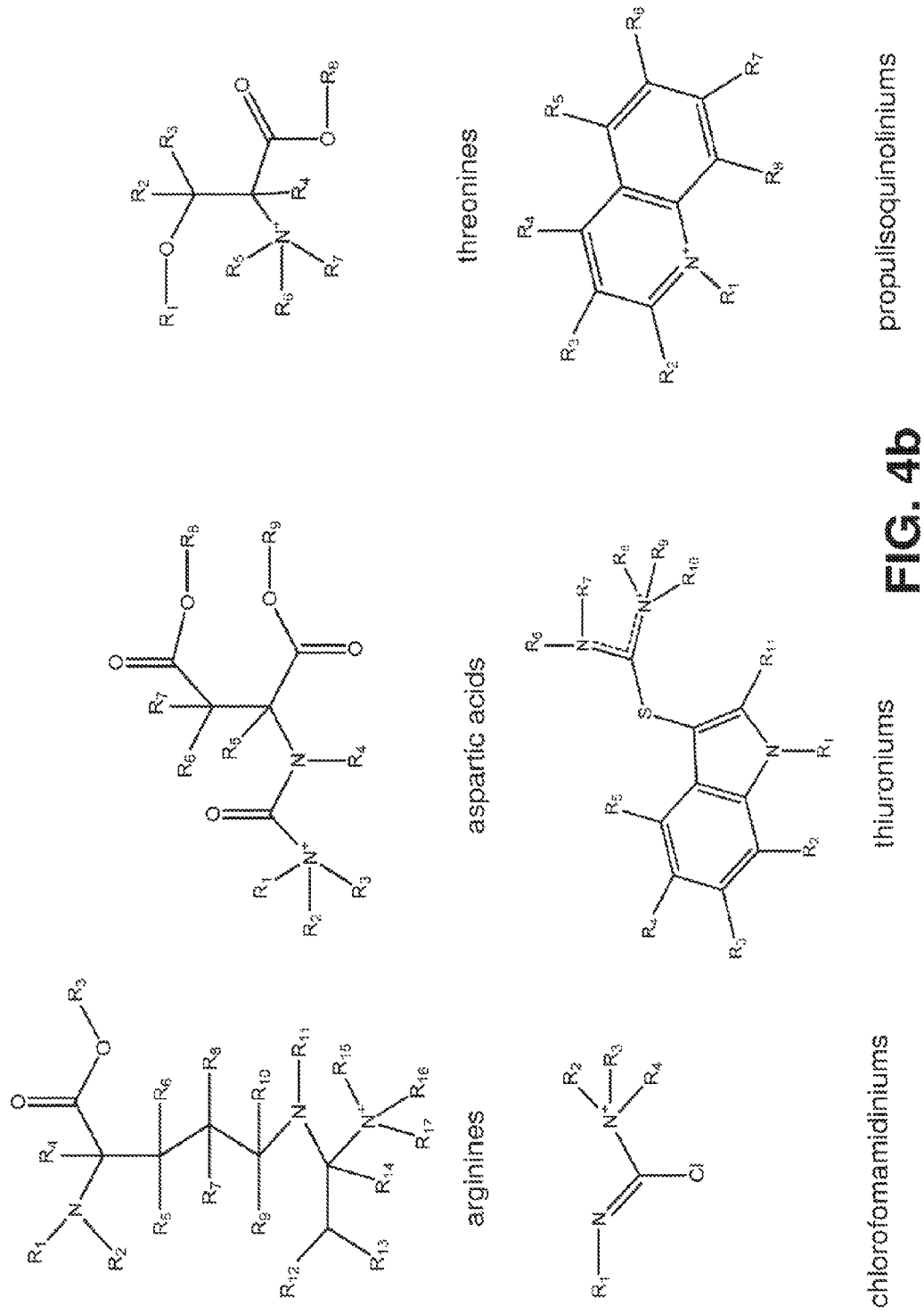
Figure 4C:
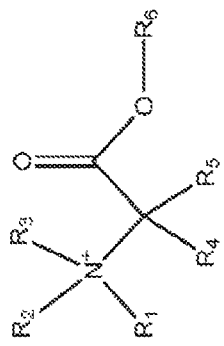
Figure 4C:
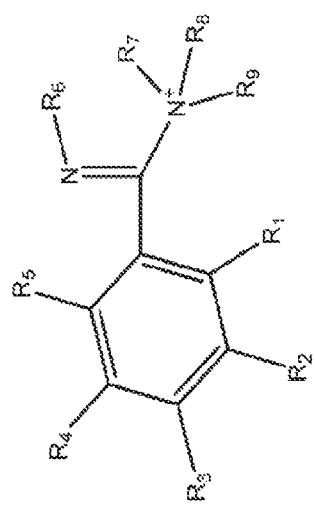
Figure 4C:
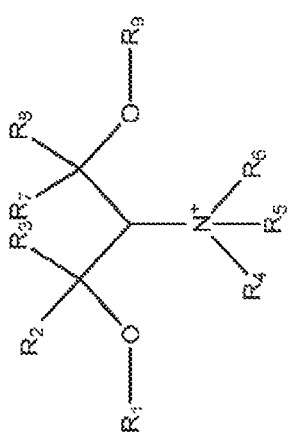
Figure 4C:
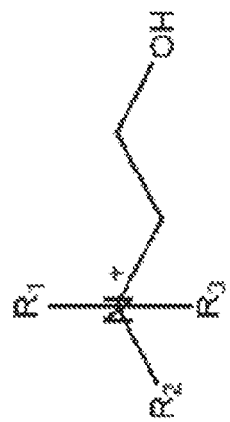
Figure 5A:
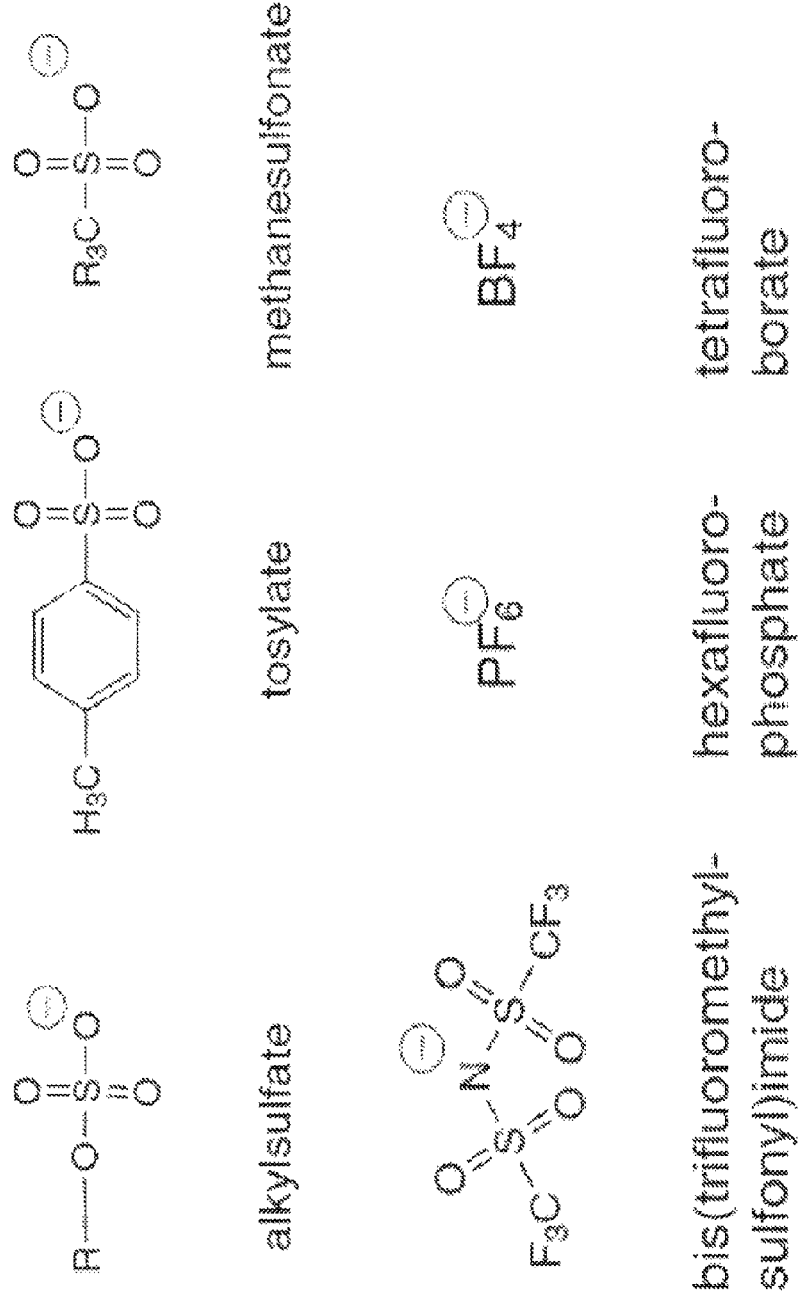
FIGS. 5a and 5b illustrate some of the anions that may help to stabilize the $(CO_2)^-$ anion.
Figure 5B:
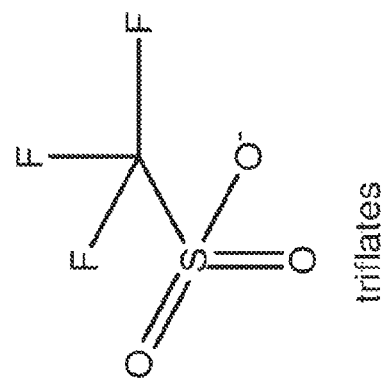
Figure 5B:
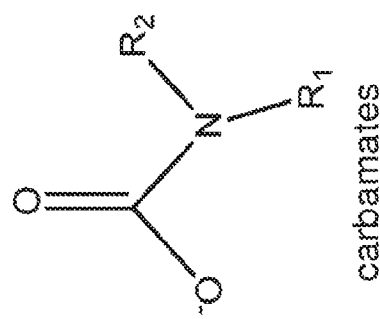
Figure 5B:
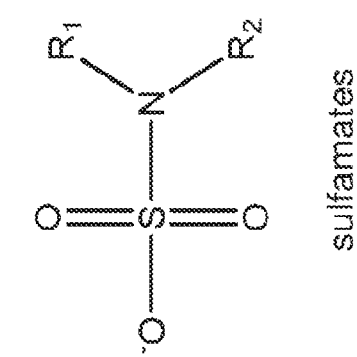

FIGS. 2 and 3 illustrate one possible mechanism by which a Helper Catalyst can enhance the rate of $CO_2$ conversion. According to Chandrasekaran, et al. (Surface Science, 185, 495-514, 1987) the high overpotentials for $CO_2$ conversion occur because the first step in the electroreduction of $CO_2$ is the formation of a $(CO_2)^-$ intermediate. It takes energy to form the intermediate as illustrated in FIG. 2. This results in a high overpotential for the reaction.

FIG. 3 illustrates what might happen if a solution containing 1-ethyl-3-methylimidazolium (EMIM$^+$) cations is added to the mixture. EMIM$^+$ might be able to form a complex with the $(CO_2)^-$ intermediate. In that case, the reaction could proceed via the EMIM$^+$-$(CO_2)^-$ complex instead of going through a bare $(CO_2)^-$ intermediate as illustrated in FIG. 3. If the energy to form the EMIM$^-$-$(CO_2)^-$ complex is less than the energy to form the $(CO_2)^-$ intermediate, the overpotential for $CO_2$ conversion could be substantially reduced. Therefore, any substance that includes EMIM$^+$ cations could act as a Helper Catalyst for $CO_2$ conversion.

In most cases, solvents only have small effects on the progress of catalytic reactions. The interaction between a solvent and an adsorbate is usually much weaker than the interaction with a Catalytically Active Element, so the solvent only makes a small perturbation to the chemistry occurring on metal surfaces. However, the diagram in FIG. 3 shows that such an effect could be large.

Of course a Helper Catalyst, alone, will be insufficient to convert $CO_2$. Instead, a Catalytically Active Element is needed that can catalyze reactions of $(CO_2)^-$ in order to get high rates of $CO_2$ conversion. Catalysts including at least one of the following Catalytically Active Elements have been previously reported to be active for electrochemical conversion of $CO_2$, namely, V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sin, Tb, La, Ce, and Nd.

Many of these catalysts also show activity for a number of other reactions. All of these elements are specifically included as Catalytically Active Elements for the purposes of the invention. This list of elements is meant for illustrative purposes only, and is not meant to limit the scope of the invention.

Further, those skilled in the art should realize that the diagram in FIG. 3 could be drawn for any molecule that could form a complex with $(CO_2)^-$. Previous literature indicates that solutions including one or more of: ionic liquids, deep eutectic solvents, amines, and phosphines; including specifically imidazoliums (also called imidazoniums), pyridiniums, pyrrolidiniums, phosphoniums, ammoniums, sulfoniums, prolinates, and methioninates can form complexes with $CO_2$. Consequently, they may serve as Helper Catalysts. Also Davis Jr., et al. (In ACS Symposium Series 856: Ionic Liquids as Green Solvents: Progress and Prospects, 100-107, 2003) list a number of other salts that show ionic properties. Specific examples include compounds including one or more of acetocholines, alanines, aminoacetonitriles, methylammoniums, arginines, aspartic acids, threonines, chloroformamidiniums, thiouroniums, quinoliniums, pyrrolidinols, serinols, benzamidines, sulfamates, acetates, carbamates, triflates, and cyanides. These salts may act as Helper Catalysts. These examples are meant for illustrative purposes only, and are not meant to limit the scope of the invention.

Of course, not every substance that forms a complex with $(CO_2)^-$ will act as a Helper Catalyst. Masel (Chemical Kinetics and Catalysis, Wiley 2001, pp. 717-720) notes that when an intermediate binds to a catalyst, the reactivity of the intermediate decreases. If the intermediate bonds too strongly to the catalyst, the intermediate will become unreactive, so the substance will not be effective. This provides a key limitation on substances that act as Helper Catalysts. The Helper Catalyst cannot form so strong a bond with the $(CO_2)^-$ that the $(CO_2)^-$ is unreactive toward the Catalytically Active Element.

More specifically, one wishes the substance to form a complex with the $(CO_2)^-$ so that the complex is stable (that is, has a negative free energy of formation) at potentials less negative than $-1$ V with respect to the standard hydrogen electrode (SHE.) However, the complex should not be so stable that the free energy of the reaction between the complex and the Catalytically Active Element is more positive than about 3 kcal/mol.

Those trained in the state of the art should realize that the ability of the Helper Catalyst to stabilize the $(CO_2)^-$ also varies with the anion. For example Zhao, et al. (The Journal of Supercritical Fluids, 32, 287-291, 2004) examined $CO_2$ conversion in 1-n-butyl-3-methylimidazolium hexafluorophosphate (BMIM-PF6), but FIG. 3 in Zhao, et al., shows that the BMIM-PF6 did NOT lower the overpotential for the reaction (that is, the BMIM-PF6 did not act as a Helper Catalyst.) This may be because the BMIM-PF6 formed such a strong bond to the $(CO_2)^-$ that the $CO_2$ was unreactive with the copper. Similarly, Yuan, et al., Electrochimica Acta 54 (2009) 2912-2915, examined the reaction between methanol and $CO_2$ in 1-butyl-3-methylimidazolium bromide (BMIM-Br). The BMIM-Br did not act as a Helper Catalyst. This may be because the complex was too weak or that the bromine poisoned the reaction.

Figure 6:
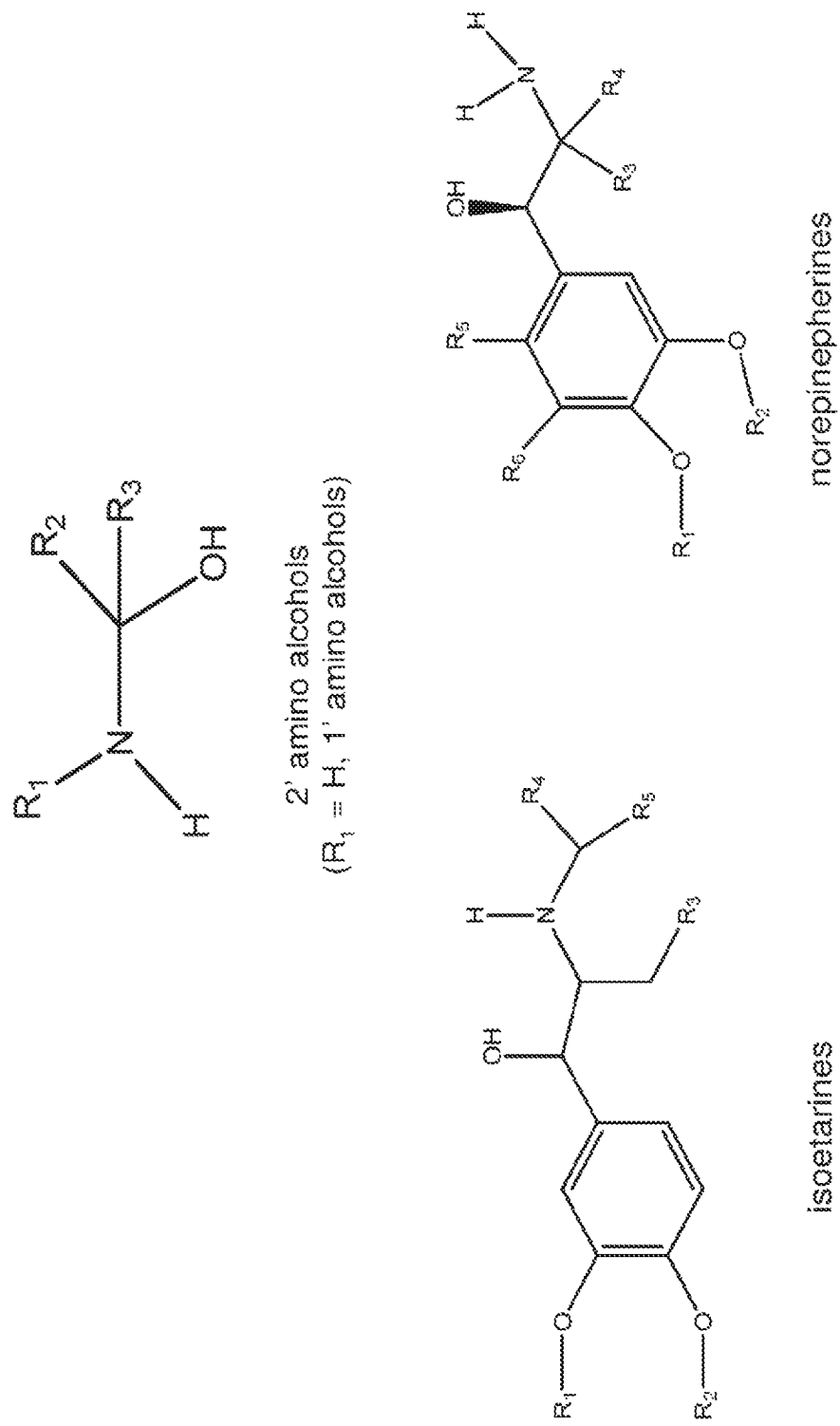
FIG. 6 illustrates some of the neutral molecules that may be used to form a complex with $(CO_2)^-$.

Solutions that include one or more of the cations in FIG. 4, the anions in FIG. 5, and/or the neutral species in FIG. 6, where R1, R2 and R3 (and R4-R17) include H, OH or any ligand containing at least on carbon atom, are believed to form complexes with $CO_2$ or $(CO_2)^-$. Specific examples include: imidazoliums (also called imidazoniums), pyridiniums, pyrrolidiniums, phosphoniums, ammoniums, sulfoniums, prolinates, and methioninates. All of these examples might be able to be used as Helper Catalysts for $CO_2$ conversion, and are specifically included in the invention. These examples are meant for illustrative purposes only, and are not meant to limit the scope of the invention.

In general one can determine whether a given substance S is a Helper Catalyst for a reaction R catalyzed by an active metal M as follows:

Fill a standard 3 electrode electrochemical cell with the electrolyte commonly used for reaction R. Common electrolytes include such as 0.1 M sulfuric acid or 0.1 M KOH in water can also be used.

Mount the active metal into the 3 electrode electrochemical cell and an appropriate counter electrode.

Run several CV cycles to clean the active metal.

Measure the reversible hydrogen electrode (RHE) potential in the electrolyte

Load the reactants for the reaction R into the cell, and measure a CV of the reaction R, noting the potential of the peak associated with the reaction R.

Calculate V1=the difference between the onset potential of the peak associated with reaction and RHE.

Calculate V1A=the difference between the maximum potential of the peak associated with reaction and RHE.

Add 0.0001 to 99.9999% of the substance S to the electrolyte.

Measure RHE in the reaction with Helper Catalyst.

Measure the CV of reaction R again, noting the potential of the peak associated with the reaction R.

Calculate V2=the difference between the onset potential of the peak associated with reaction and RHE.

Calculate V2A=the difference between the maximum potential of the peak associated with reaction and RHE.

If V2<V1 or V2A<V1A at any concentration of the substance S between 0.0001 and 99.9999%, the substance S is a Helper Catalyst for the reaction.

Further, the Helper Catalyst could be in any one of the following forms: (i) a solvent for the reaction; (ii) an electrolyte; (iii) an additive to any component of the system; (iv) something that is bound to at least one of the catalysts in a system, (v) a polymer. These examples are meant for illustrative purposes only, and are not meant to limit the scope of the invention.

Those trained in the state of the art should recognize that one might only need a tiny amount of the Helper Catalyst to have a significant effect. Catalytic reactions often occur on distinct active sites. The active site concentration can be very low, so in principle a small amount of Helper Catalyst can have a significant effect on the rate. One can obtain an estimate of how little of the Helper Catalyst would be needed to change the reaction from Pease, et al., JACS 47, 1235 (1925) study of the effect of carbon monoxide (CO) on the rate of ethylene hydrogenation on copper. This paper is incorporated into this disclosure by reference. Pease, et al., found that 0.05 cc's (62 micrograms) of carbon monoxide (CO) was sufficient to almost completely poison a 100 grain catalyst towards ethylene hydrogenation. This corresponds to a poison concentration of 0.0000062% by weight of CO in the catalyst. Those trained in the state of the art know that if 0.0000062% by weight of the poison in a Catalytically Active Element-poison mixture could effectively suppress a reaction, then as little as 0.0000062% by weight of Helper Catalyst in an Active Element, Helper Catalyst Mixture could enhance a reaction. This provides an estimate of a lower limit to the Helper Catalyst concentration in an Active Element, Helper Catalyst Mixture.

The upper limit is illustrated in Example 1 below, where the Active Element, Helper Catalyst Mixture could have approximately 99.999% by weight of Helper Catalyst, and the Helper Catalyst could be at least an order of magnitude more concentrated. Thus the range of Helper Catalyst concentrations for the invention here may be 0.0000062% to 99.9999% by weight.

FIG. 3 only considered the electrochemical conversion of $CO_2$, but the method is general. There are many examples where energy is needed to create a key intermediate in a reaction sequence. Examples include: homogeneously catalyzed reactions, heterogeneously catalyzed reactions, chemical reactions in chemical plants, chemical reactions in power plants, chemical reactions in pollution control equipment and devices, chemical reactions in safety equipment, chemical reactions in fuel cells, and chemical reactions in sensors. Theoretically, if one could find a Helper Catalyst that forms a complex with a key intermediate, the rate of the reaction should increase. All of these examples are within the scope of the invention.

Specific examples of specific processes that may benefit with Helper Catalysts include the electrochemical process to produce products including one or more of $Cl_2$, $Br_2$, $I_2$, NaOH, KOH, NaClO, $NaClO_3$, $KClO_3$, $CF_3COOH$.

Further, the Helper Catalyst could enhance the rate of a reaction even if it does not form a complex with a key intermediate. Examples of possible mechanisms of action include the Helper Catalyst (i) lowering the energy to form a key intermediate by any means, (ii) donating or accepting electrons or atoms or ligands, (iii) weakening bonds or otherwise making them easier to break, (iv) stabilizing excited states, (v) stabilizing transition states, (vi) holding the reactants in close proximity or in the right configuration to react, or (vii) blocking side reactions. Each of these mechanisms is described on pages 707 to 742 of Masel, Chemical Kinetics and Catalysis, Wiley, N.Y. (2001). All of these modes of action are within the scope of the invention.

Also, the invention is not limited to just the catalyst. Instead it includes any process or device that uses an Active Element, Helper Catalyst Mixture as a catalyst. Fuel cells are sensors are specifically included in the invention.

Without further elaboration, it is believed that one skilled in the art using the preceding description can utilize the invention to the fullest extent. The following examples are illustrative only, and not limiting of the disclosure in any way whatsoever. These are merely illustrative and are not meant to be an exhaustive list of all possible embodiments, applications or modifications of the invention.

Specific Example 1

Figure 7:
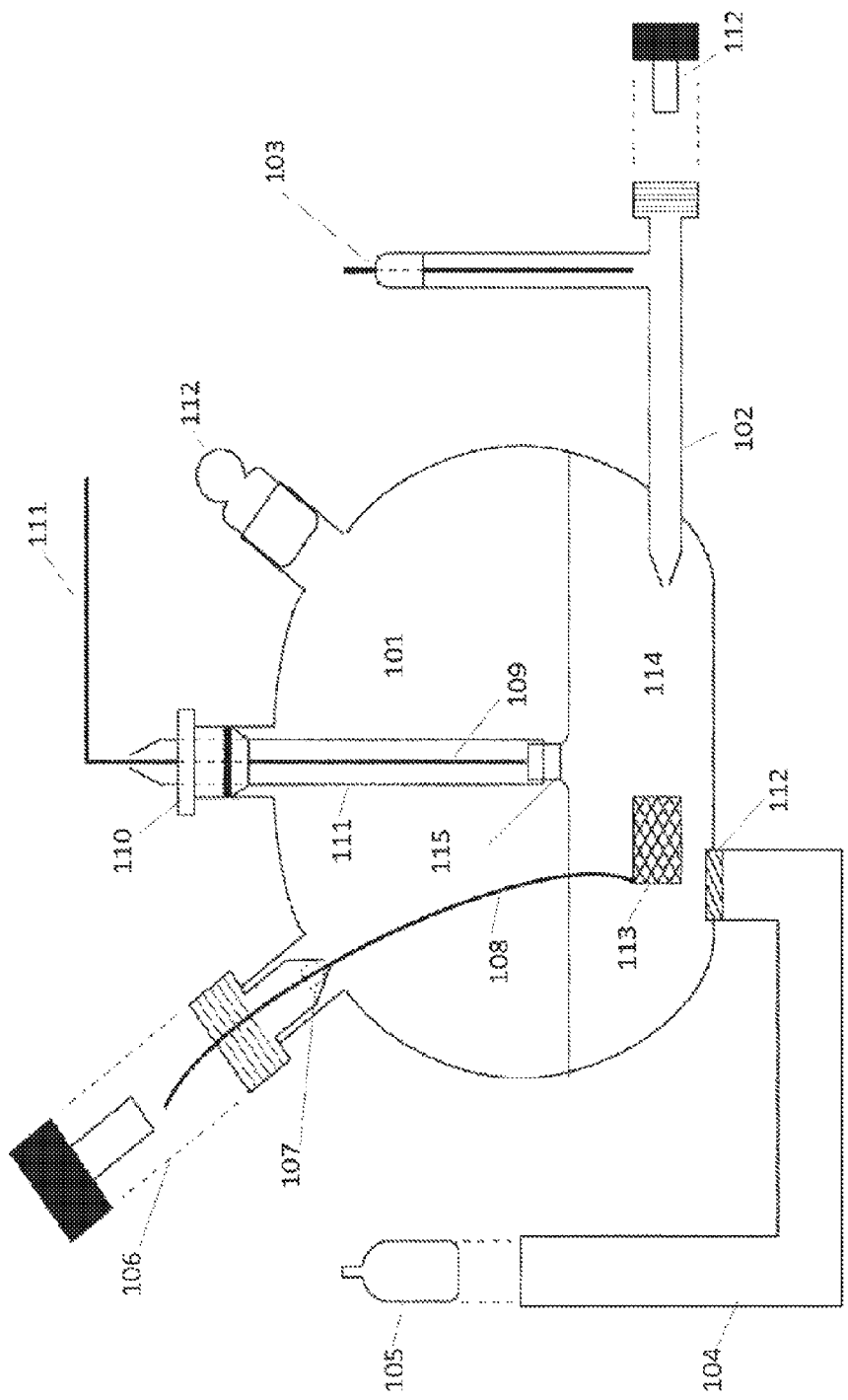
FIG. 7 shows a schematic of a cell used for the experiments in Examples 1, 2, 3, 4 and 5.

Using an Active Element, Helper Catalyst Mixture Including Platinum and 1-Ethyl-3-Methylimidazolium Tetrafluoroborate (EMIM-BF4) to Lower the Overpotential for Electrochemical Conversion of $CO_2$ and Raise the Selectivity (Current Efficiency) of the Reaction The experiments employed the glass three electrode cell shown in FIG. 7. The cell consisted of a three neck flask 101, to hold the anode 108, and the cathode 109. A silver/0.01 molar silver ion reference electrode 103 in acetonitrile was connected to the cell through a Luggin Capillary 102. The reference electrode 103 was fitted with a Vycor® frit to prevent any of the reference electrode solution from contaminating the ionic liquid in the capillary. The reference electrode was calibrated against the ferrocene Fc/Fc+ redox couple. A conversion factor of +535 was used to convert our potential axis to reference the Standard Hydrogen Electrode (SHE). A 25×25 mm platinum gauze (size 52) 113 was connected to the anode while a 0.33 $cm^2$ polycrystalline gold plug 115 was connected to the cathode.

Prior to the experiments all glass parts were put through a 1% Nochromix® bath (2 hours), followed by a 50/50 v/v Nitric Acid/Water bath (12 hours), followed by rinsing with Millipore water. In addition, the gold plug 115 and platinum gauze 113 were mechanically polished using procedures known to workers trained in the art. They were then cleaned in a sulfuric acid bath for 12 hours.

During the experiment a catalyst ink comprising a Catalytically Active Element, platinum, was first prepared as follows: First 0.056 grains of Johnson-Matthey Hispec 1000 platinum black purchased from Alfa-Aesar was mixed with 1 gram of Millipore water and sonicated for 10 minutes to produce a solution containing a 5.6 mg/ml suspension of platinum black in Millipore water. A 25 µl drop of the ink was placed on the gold plug 115 and allowed to dry under a heat lamp for 20 min, and subsequently allowed to dry in air for an additional hour. This yielded a catalyst with 0.00014 grams of Catalytically Active Element, platinum, on a gold plug. The gold plug was mounted into the three neck flask 101. Next a Helper Catalyst, EMIM-BF4 (EMD Chemicals, Inc., San Diego, Calif., USA) was heated to 120° C. under a −23 in. Hg vacuum for 12 hours to remove residual water and oxygen. The concentration of water in the ionic liquid after this procedure was found to be ca. 90 mM by conducting a Karl-Fischer titration. (That is, the ionic liquid contained 99.9999% of Helper Catalyst.) 13 grains of the EMIM-BF4 was added to the vessel, creating an Active Element, Helper Catalyst Mixture that contained about 99.999% of the Helper Catalyst. The geometry was such that the gold plug formed a meniscus with the EMIM-BF4. Next, ultra-high-purity (UHP) argon was fed through the sparging tube 104 and glass frit 112 for 2 hours at 200 sccm to further remove any moisture picked up by contact with the air.

Next the cathode was connected to the working electrode connection in an SI 1287 Solartron electrical interface, the anode was connected to the counter electrode connection and the reference electrode was connected to the reference electrode connection on the Solartron. Then the potential on the cathode was swept from −1.5 V versus a standard hydrogen electrode (SHE) to 1 V vs. SHE, and then back to −1.5 volts versus SHE thirty times at a scan rate of 50 mV/s. The current produced during the last scan is labeled as the "argon" scan in FIG. 8.

Next carbon dioxide was bubbled through the sparging tube at 200 sccm for 30 minutes, and the same scanning technique was used. That produced the $CO_2$ scan in FIG. 8. Notice the peak starting at −0.2 volts with respect to SHE, and reaching a maximum at −0.4 V with respect to SHE. That peak is associated with $CO_2$ conversion.

We have also used broad-band sum frequency generation (BB-SFG) spectroscopy to look for products of the reaction. We only detect our desired product carbon monoxide in the voltage range shown (namely, the selectivity is about 100%). Oxalic acid is detected at higher potentials.

Table 1 compares these results to results from the previous literature. The table shows the actual cathode potential.

More negative cathode potentials correspond to higher overpotentials. More precisely the overpotential is the difference between the thermodynamic potential for the reaction (about −0.2 V with respect to SHE) and the actual cathode potential. The values of the cathode overpotential are also given in the table. Notice that the addition of the Helper Catalyst has reduced the cathode overpotential (namely, lost work) on platinum by a factor of 4.5 and improved the selectivity to nearly 100%.

TABLE 1

(Comparison of Data in Example 1 to Results Reported in Previous Literature)

| Reference | Catalytically Active Element | Cathode potential versus SHE | Cathode overpotential | Selectivity to carbon-containing products |
|---|---|---|---|---|
| Data from Example 1 | Platinum (+EMIM-BF$_4$) | −0.4 V | 0.2 V | ~100% |
| Hori Review Table 3 | Platinum (+water) | −1.07 V | 0.87 V | 0.1% |
| The Li and Oloman papers and the '727 application | Tin | −2.5 to −3.2 V | 2.3 to 3 V | 40-70% |

TABLE 2

(Cathode Potentials Where $CO_2$ Conversion Starts on a Number of Catalytically Active Elements as Reported in the Hori Review)

| Metal | Cathode potential (SHE) | Metal | Cathode potential (SHE) | Metal | Cathode potential (SHE) |
|---|---|---|---|---|---|
| Pb | −1.63 | Hg | −1.51 | Tl | −1.60 |
| In | −1.55 | Sn | −1.48 | Cd | −1.63 |
| Bi | −1.56 | Au | −1.14 | Ag | −1.37 |
| Zn | −1.54 | Pd | −1.20 | Ga | −1.24 |
| Cu | −1.44 | Ni | −1.48 | Fe | −0.91 |
| Pt | −1.07 | Ti | −1.60 | | |

Figure 8:
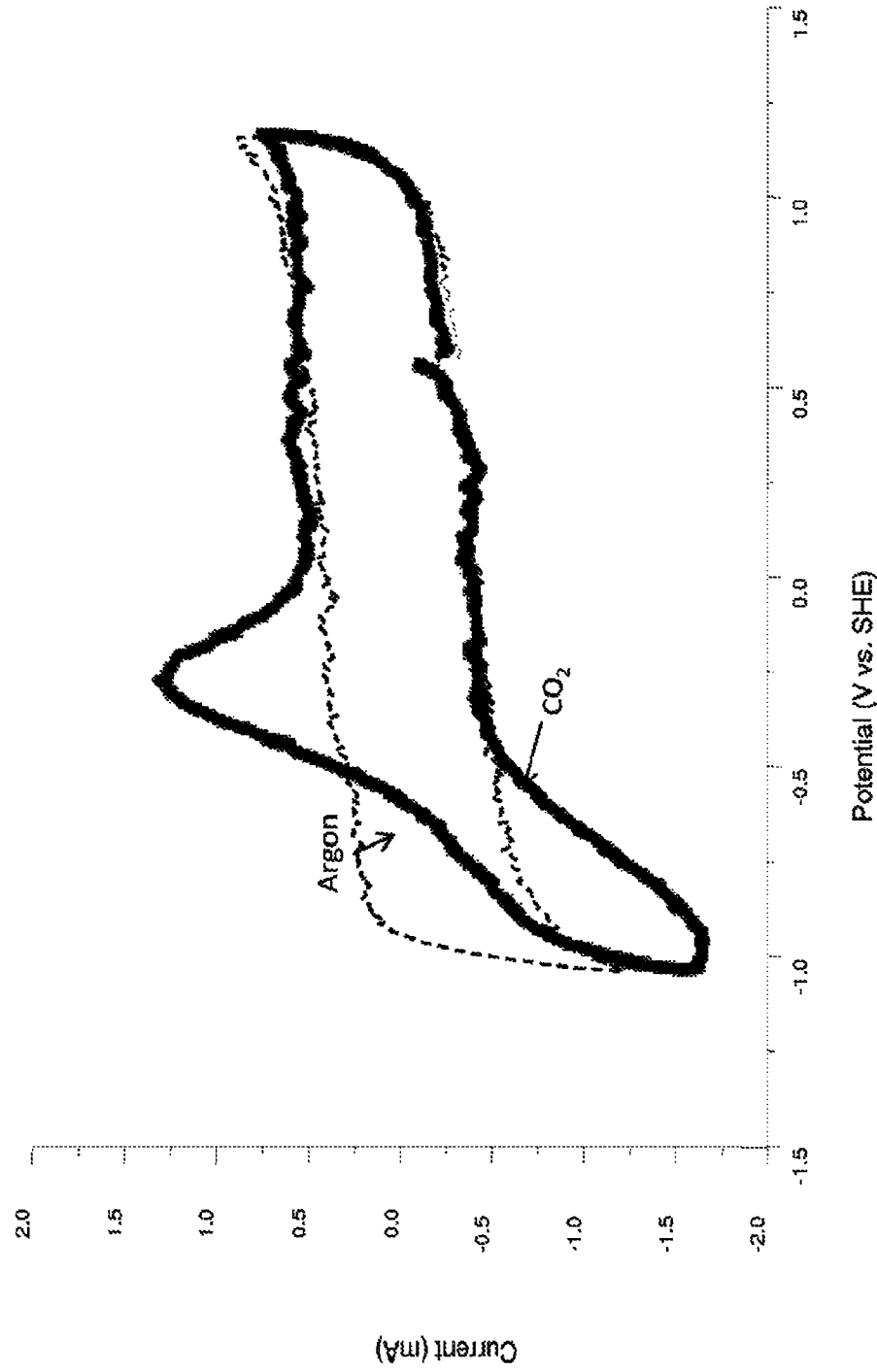
FIG. 8 represents a comparison of the cyclic voltammetry for a blank scan where the catalyst was synthesized as in Example 1 where (i) the EMIM-BF4 was sparged with argon, and (ii) a scan where the EMIM-BF4 was sparged with $CO_2$. Notice the large negative peak associated with $CO_2$ complex formation.

Table 2 indicates the cathode potential needed to convert $CO_2$. Notice that all of the values are more negative than −0.9 V. By comparison, FIG. 8 shows that $CO_2$ conversion starts at −0.2 V with respect to the reversible hydrogen electrode (RHE) when the Active Element, Helper Catalyst Mixture is used as a catalyst. More negative cathode potentials correspond to higher overpotentials. This is further confirmation that Active Element, Helper Catalyst Mixtures are advantageous for $CO_2$ conversion.

Figure 9:
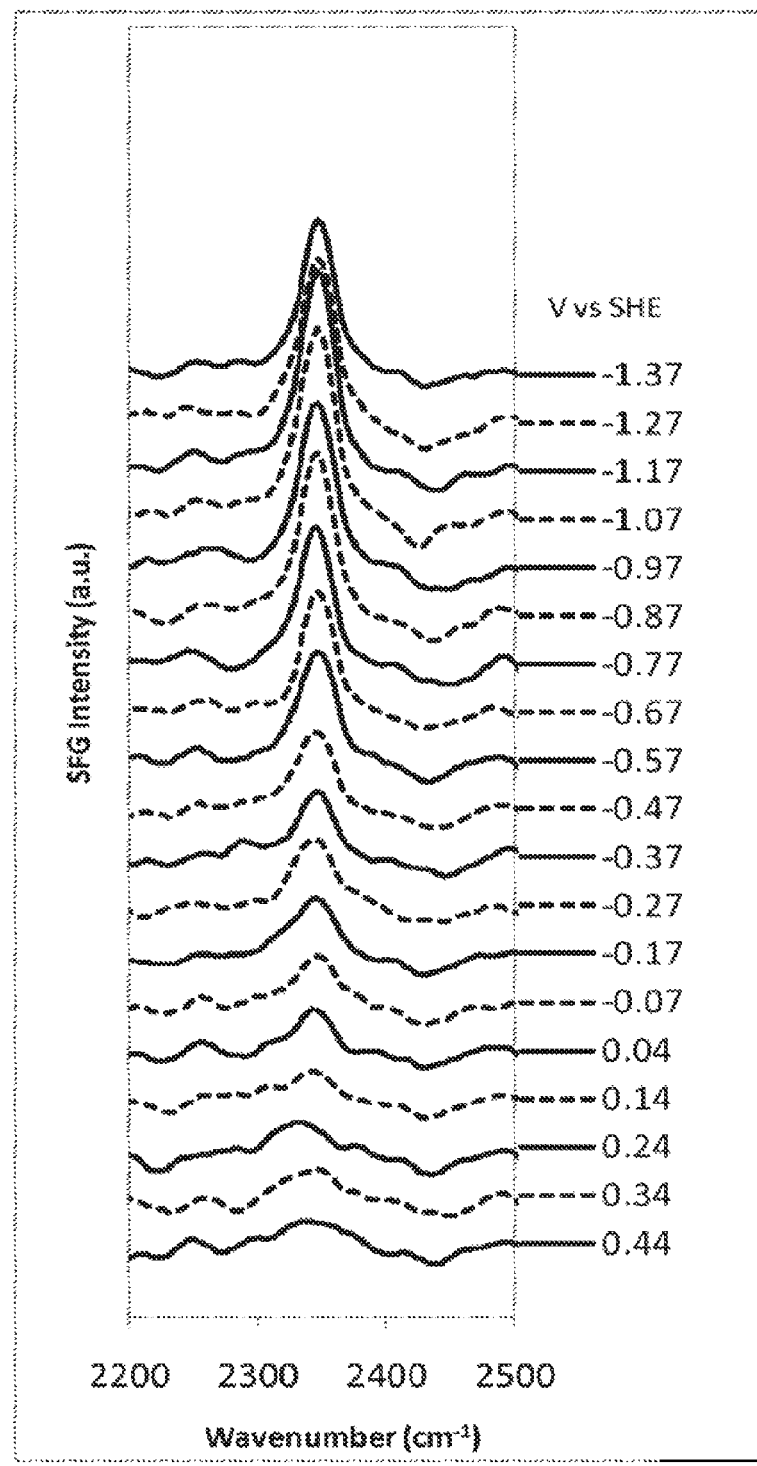
FIG. 9 represents a series of Broad Band Sum Frequency Generation (BB-SFG) spectra taken sequentially as the potential in the cell was scanned from +0.0 to −1.2 with respect to SHE.

FIG. 9 shows a series of BB-SFG spectra taken during the reaction. Notice the peak at 2350 cm-1. This peak corresponded to the formation of a stable complex between the Helper Catalyst and $(CO_2)^-$. It is significant that the peak starts at −0.1 V with respect to SHE. According to the Hori Review, $(CO_2)^-$ is thermodynamically unstable unless the potential is more negative than −1.2 V with respect to SHE on platinum. Yet FIG. 9 shows that the complex between EMIM-BF4 and $(CO_2)^-$ is stable at −0.1 V with respect to SHE.

Those trained in the art should recognize that this result is very significant. According to the Hori Review, the Dubois Review and references therein, the formation of $(CO_2)^-$ is the rate determining step in $CO_2$ conversion to CO, OH—, HCO—, $H_2CO$, $(HCO_2)$—, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sin, Tb, La, Ce, and Nd. The $(CO_2)^-$ is thermodynamically unstable at low potentials, which leads to a high overpotential for the reaction as indicated in FIG. 2. The data in FIG. 9 shows that one can form the EMIM-BF4-$(CO_2)^-$ complex at low potentials. Thus, the reaction can follow a low energy pathway for $CO_2$ conversion to CO, OH$^-$, HCO$^-$, $H_2CO$, $(HCO_2)^-$, $H_2CO_2$, $CH_3OH$, $CH_4$, $C_2H_4$, $CH_3CH_2OH$, $CH_3COO$, $CH_3COOH$, $C_2H_6$, $O_2$, $H_2$, $(COOH)_2$, or $(COO)_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Ti, Pb, Bi, Sb, Te, U, Sin, Tb, La, Ce, and Nd as indicated in FIG. 3.

In order to understand the economic consequences of this result, we calculated the cost of the electricity needed to create 100,000 metric tons per year of formic acid via two processes, (i) the process described in The Li and Oloman papers and the '727 application, and (ii) a similar process using the catalyst in this example. In both cases we assumed that the anode would run at +1.2 V with respect to SHE and that electricity would cost $0.06/kW-hr, and we scaled the current to be reasonable. The results of the calculations are given in Table 3. Notice that the calculations predict that the electricity cost will go down by almost a factor of 5 if the new catalysts are used. These results demonstrate the possible impact of the new catalysts disclosed here.

TABLE 3

(Comparison of the projected costs using catalyst in Li and Oloman papers and the '727 application, and a similar process using the catalyst in this example)

| Catalyst | Cathode potential, V (SHE) | Anode Potential, V (SHE) | Net Potential V | Selectivity | Yearly Electricity cost |
|---|---|---|---|---|---|
| The Li and Oloman papers and the '727 application | −3.2 | 1.2 | 4.4 | 0.6 | $65,000,000 |
| Active Element, Helper Catalyst Mixture | −0.4 | 1.2 | 1.6 | 1 | $14,000,000 |

Specific Example 2

The Effect of Dilution on the Electrochemical Conversion of $CO_2$

Figure 10:
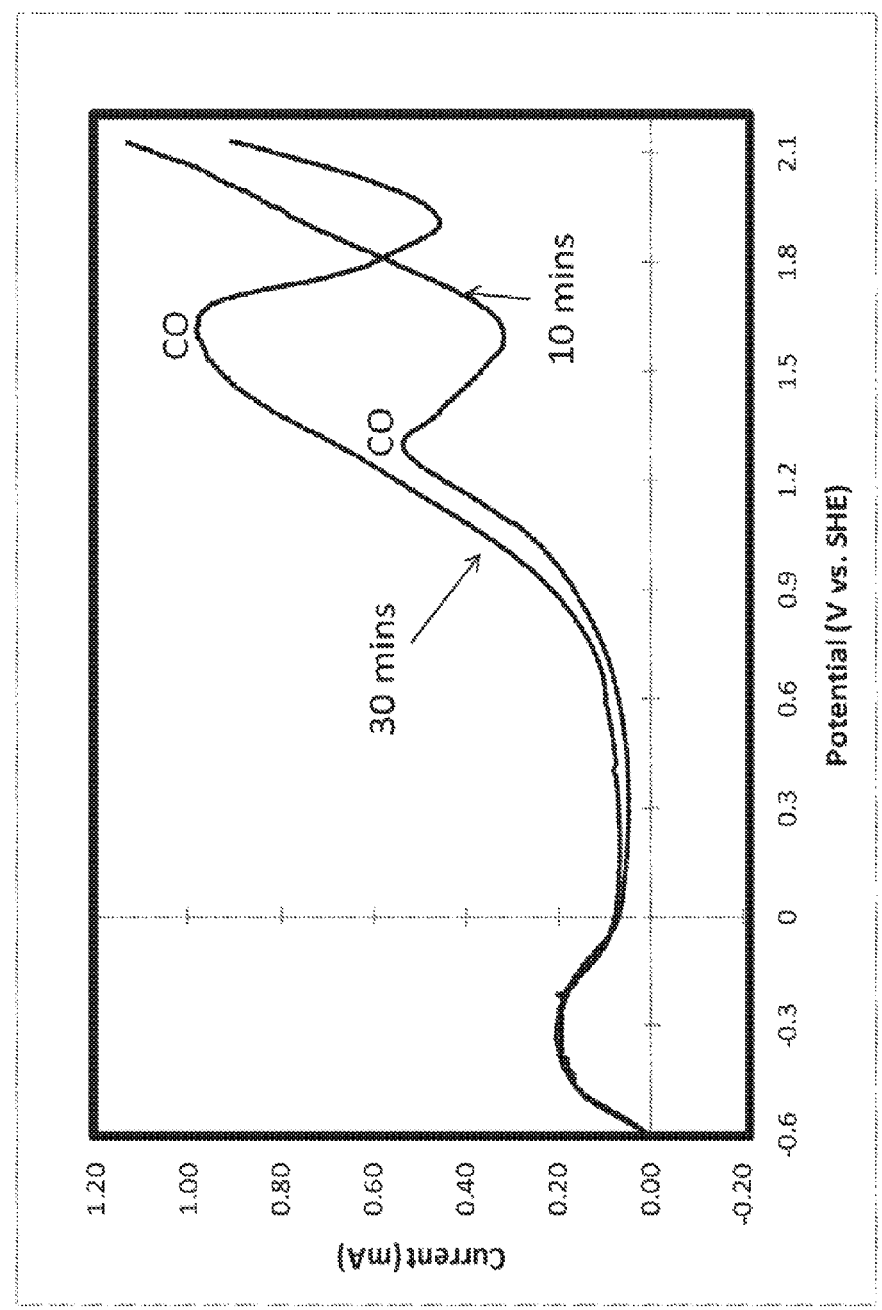
FIG. 10 shows a CO stripping experiment done by holding the potential at −0.6 V for 10 or 30 minutes and then measuring the size of the CO stripping peak between 1.2 and 1.5 V with respect to RHE.

This example shows that water additions speed the formation of CO. The experiment used the Cell and procedures in Example 1, with the following exception: a solution containing 98.55% EMIM-BF4 and 0.45% water was substituted for the 99.9999% EMIM-BF4 used in Example 1, the potential was held for 10 or 30 minutes at −0.6 V with respect to RHE, and then the potential was ramped positively at 50 mV/sec. FIG. 10 shows the result. Notice the peak between 1.2 and 1.5 V. This is the peak associated with CO formation and is much larger than in Example 1. Thus the addition of water has accelerated the formation of CO presumably by acting as a reactant.

Specific Example 3

Using an Active Element, Helper Catalyst Mixture Including Palladium and Choline Iodide to $CO_2$ Lower the Overpotential for Electrochemical Conversion of $CO_2$ in Water The next example is to demonstrate that the invention can be practiced using palladium as an Active Element and choline iodide as a Helper Catalyst.

The experiment used the Cell and procedures in Example 1, with the following exceptions: (i) a 10.3% by weight of a Helper Catalyst, choline iodide, in water solution was substituted for the 1-ethyl-3-methylimidazolium tetrafluoroborate and (ii) a 0.25 $cm^2$ Pd foil purchased from Alfa Aesar of Ward Hill, Mass., USA, was substituted for the gold plug and platinum black on the cathode, and a silver/silver chloride reference was used.

The cell contained 52 mg of palladium and 103 mg of Helper Catalyst, so the overall catalyst mixture contained 66% of Helper Catalyst.

Figure 11:
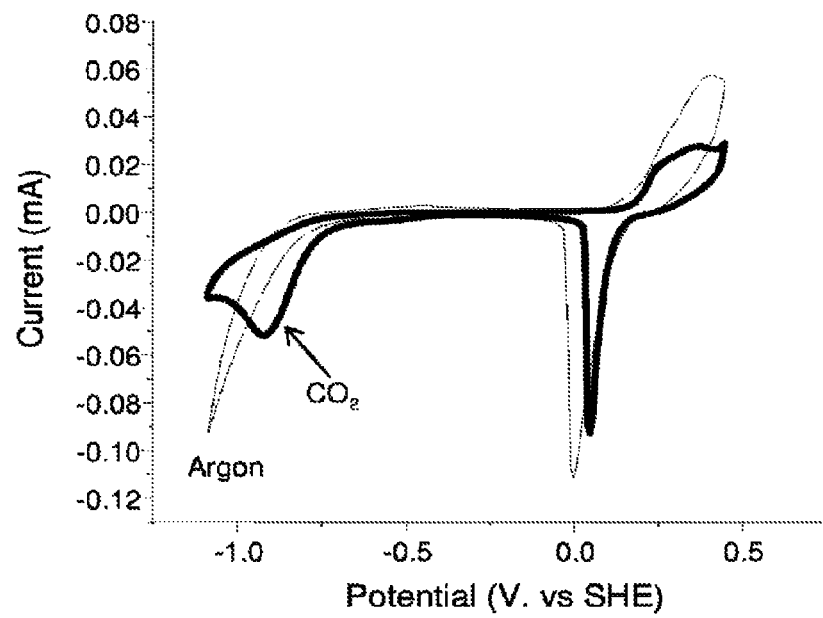
FIG. 11 represents a comparison of the cyclic voltammetry for a blank scan where the catalyst was synthesized as in Example 3 where (i) the water-choline iodide mixture was sparged with argon and (ii) a scan where the water-choline iodide mixture was sparged with $CO_2$.

FIG. 11 shows a CV taken under these conditions. There is a large negative peak near zero volts with respect to SHE associated with iodine transformations and a negative going peak at about 0.8 V associated with conversion of $CO_2$. By comparison the data in Table 2 indicates that one needs to use a voltage more negative than −1.2 V to convert $CO_2$ on palladium in the absence of the Helper Catalyst. Thus, the Helper Catalyst has lowered the overpotential for $CO_2$ formation by about 0.5 V.

This example also demonstrates that the invention can be practiced with a second Active Element, palladium, and a second Helper Catalyst, choline iodide. Further, those trained in the state of the art will note that there is nothing special about the choice of palladium and choline iodide. Rather, this example shows that the results are general and not limited to the special case in Example 1.

Specific Example 4

Using an Active Element, Helper Catalyst Mixture that Includes Palladium and Choline Chloride to Lower the Overpotential for Electrochemical Conversion of $CO_2$ to Formic Acid The next example is to demonstrate that the invention can be practiced using a third Helper Catalyst, choline chloride.

The experiment used the Cell and procedures in Example 3, with the following exception: a 6.5% by weight choline chloride in water solution was substituted for the choline iodide solution.

Figure 12:
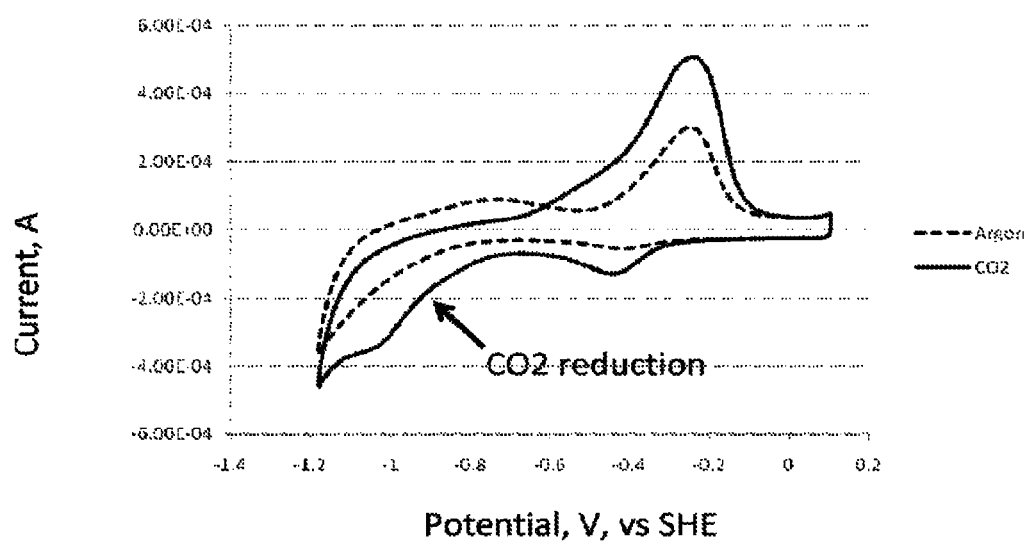
FIG. 12 shows a comparison of the cyclic voltammetry for a blank scan where the catalyst was synthesized as in Example 4 where (i) the water-choline chloride mixture was sparged with argon and (ii) a scan where the water-choline chloride mixture was sparged with $CO_2$.

The cell contained 52 mg of palladium and 65 mg of Helper Catalyst, so the overall catalyst mixture contained 51% of Helper Catalyst. FIG. 12 shows a comparison of the cyclic voltammetry for a blank scan where (i) the water-choline chloride mixture was sparged with argon and (ii) a scan where the water-choline chloride mixture was sparged with $CO_2$. Notice the negative going peaks starting at about −0.6. This shows that $CO_2$ is being reduced at −0.6 V. By comparison the data in Table 2 indicates that a voltage more negative than −1.2 V is needed to convert $CO_2$ on palladium in the absence of the Helper Catalyst. Thus, the overpotential for $CO_2$ conversion has been lowered by 0.6 V by the Helper Catalyst.

Another important point is that there is no strong peak for hydrogen formation. A bare palladium catalyst would produce a large hydrogen peak at about −0.4 V at a pH of 7, while the hydrogen peak moves to −1.2 V in the presence of the Helper Catalyst. The Hori Review reports that palladium is not an effective catalyst for $CO_2$ reduction because the side reaction producing hydrogen is too large. The data in FIG. 12 show that the Helper Catalysts are effective in suppressing hydrogen formation.

We have also used CV to analyze the reaction products. Formic acid was the only product detected. By comparison, the Hori Review reports that the reaction is only 2.8% selective to formic acid in water. Thus the Helper Catalyst has substantially improved the selectivity of the reaction to formic acid.

This example also demonstrates that the invention can be practiced with a third Helper Catalyst, choline chloride. Further, those trained in the state of the art will note that there is nothing special about the choice of palladium and choline chloride. Rather, this example shows that the results are general and not limited to the special case in Example 1.

Further, those trained in the state of art should recognize that the results should not depend on the thickness of the palladium foil. For example, if we increase the thickness of the palladium foil by a factor of 10, the Active Element-Helper Catalyst mixture would only contain 11% of Helper Catalyst. If the foil thickness is increased to 0.5 inches, the mixture will contain about 1% of Helper Catalyst.

Specific Example 5

Using an Active Element, Helper Catalyst Mixture that Includes Nickel and Choline Chloride to Lower the Overpotential for Electrochemical Conversion of $CO_2$ to CO The next example is to demonstrate that the invention can be practiced using a third metal, nickel.

The experiment used the Cell and procedures in Example 4, with the following exception: a nickel foil from Alfa Aesar was substituted for the palladium foil.

Figure 13:
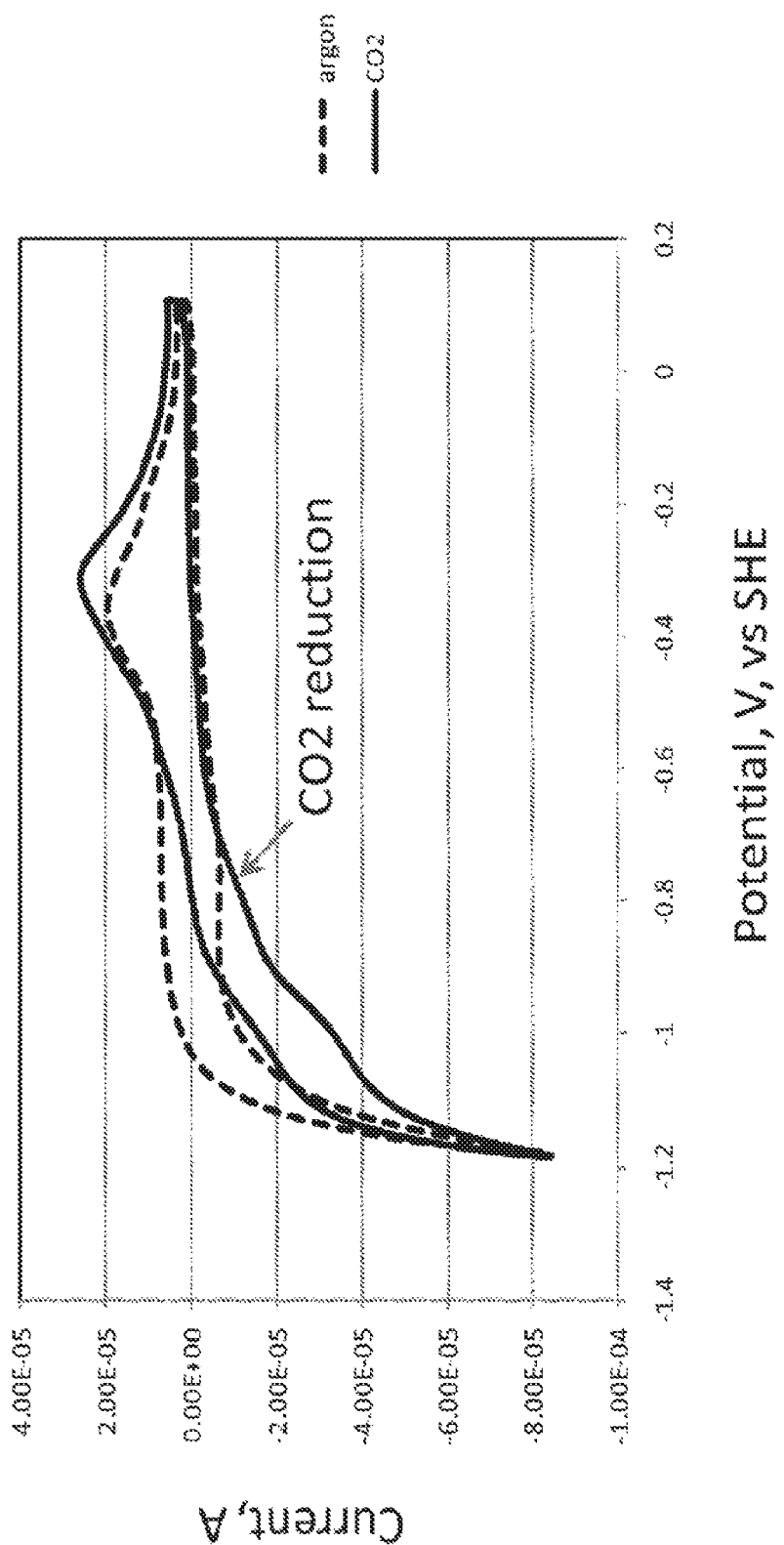
FIG. 13 shows a comparison of the cyclic voltammetry for a blank scan where the catalyst was synthesized as in Example 5 where (i) the water-choline chloride mixture was sparged with argon and (ii) a scan where the water-choline chloride mixture was sparged with $CO_2$.

FIG. 13 shows a comparison of the cyclic voltammetry for a blank scan where (i) the water-choline chloride mixture was sparged with argon and (ii) a scan where the water-choline chloride mixture was sparged with $CO_2$. Notice the negative going peaks starting at about −0.6. This shows that $CO_2$ is being reduced at −0.6 V. By comparison, the data in Table 2 indicates that a voltage more negative than −1.48 V is needed to convert $CO_2$ on nickel in the absence of the Helper Catalyst. Thus, the Helper Catalyst has lowered the overpotential for $CO_2$ conversion.

Another important point is that there is no strong peak for hydrogen formation. A bare nickel catalyst would produce a large hydrogen peak at about −0.4 V at a pH of 7, while the hydrogen peak moves to −1.2 V in the presence of the Helper Catalyst. The Hori Review reports that nickel is not an effective catalyst for $CO_2$ reduction because the side reaction producing hydrogen is too large. The data in FIG. 13 show that the Helper Catalysts are effective in suppressing hydrogen formation.

Also the Helper Catalyst is very effective in improving the selectivity of the reaction. The Hori Review reports that hydrogen is the major product during carbon dioxide reduction on nickel in aqueous solutions. The hydrolysis shows 1.4% selectivity to formic acid, and no selectivity to carbon monoxide. By comparison, analysis of the reaction products by CV indicates that carbon monoxide is the major product during $CO_2$ conversion on nickel in the presence of the Helper Catalyst. There may be some formate formation. However, no hydrogen is detected. This example shows that the Helper Catalyst has tremendously enhanced the selectivity of the reaction toward CO and formate.

This example also demonstrates that the invention can be practiced with a third metal, nickel. Further, those trained in the state of the art will note that there is nothing special about the choice of nickel and choline chloride. Rather, this example shows that the results are general and not limited to the special case in Example 1.

Those trained in the state of art should realize that since choline chloride and choline iodide are active, other choline salts such as choline bromide, choline fluoride and choline acetate should be active too.

Specific Example 6

Demonstration that an Active Element (Gold), Helper Catalyst Mixture is Useful in a $CO_2$ Sensor This example demonstrates that the invention can be practiced with a fourth Active Element, gold. It also demonstrates that the catalysts are useful in sensors.

The sensor may be a simple electrochemical device wherein an Active Element, Helper Catalyst Mixture is placed on an anode and cathode in an electrochemical device, then the resistance of the sensor is measured. If there is no $CO_2$ present, the resistance will be high, but preferably not infinite, because of leakage currents. When $CO_2$ is present, the Active Element, Helper Catalyst Mixture may catalyze the conversion of $CO_2$. That allows more current to flow through the sensor. Consequently, the sensor resistance decreases. As a result, the sensor may be used to detect carbon dioxide.

Figure 14:
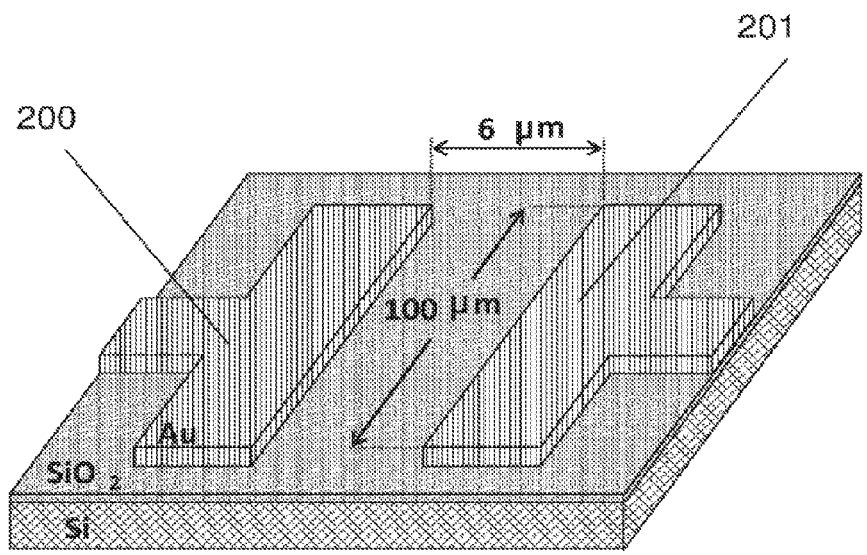
FIG. 14 shows a schematic of an example sensor before the Helper Catalyst was added.

An example sensor was fabricated on a substrate made from a 100 mm silicon wafer (Silicon Quest International, Inc., Santa Clara, Calif., USA, 500 µm thick, <100> oriented, 1-5 Ω-cm nominal resistivity) which was purchased with a 500 nm thermal oxide layer. On the wafer, 170 Å of chromium was deposited by DC magnetron sputtering ($\sim 10^{-2}$ Torr of argon background pressure). Next, 1000 Å of a Catalytically Active Element, gold, was deposited on the chromium and the electrode was patterned via a standard lift-off photolithography process to yield the device shown schematically in FIG. 14.

At this point, the device consisted of an anode 200 and cathode 201 separated by a 6 µm gap, wherein the anode and cathode were coated with a Catalytically Active Element, gold. At this point the sensor could not detect $CO_2$.

Figure 15:
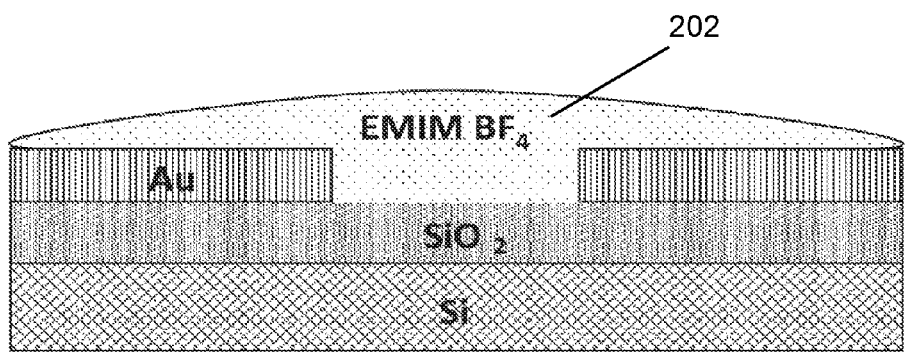
FIG. 15 shows a schematic of where EMIM BF4 is placed on the sensor.

Next 2 µl of a Helper Catalyst, EMIM BF4 202 was added over the junction as shown in FIG. 15. The device was mounted into a sensor test cell with wires running from the anode and cathode.

Figure 16:
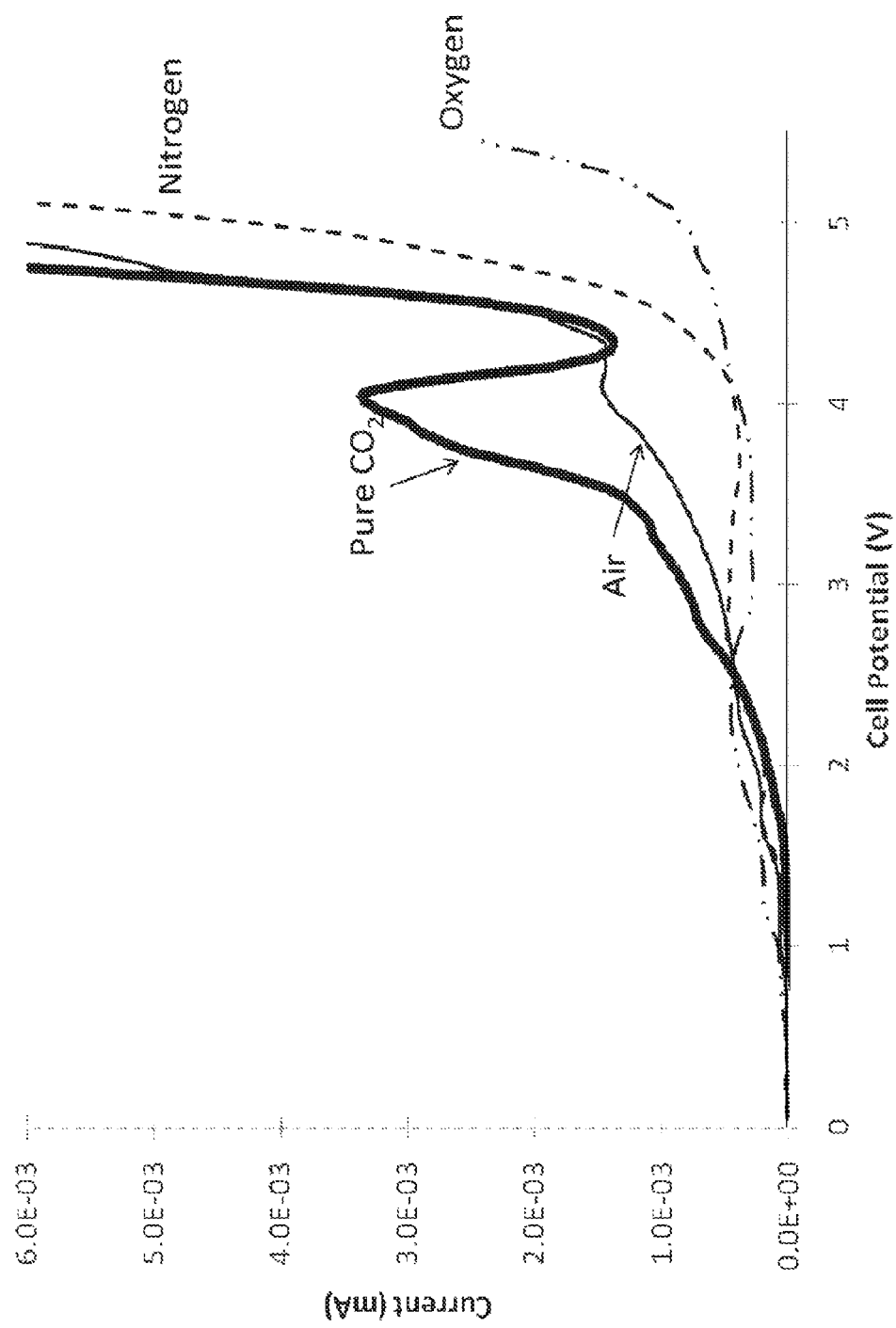
FIG. 16 represents the current measured when the voltage on the sensor was exposed to various gases; the applied voltage on the sensor was swept from 0 to 5 volts at 0.1 V/sec.

Next, the anode and cathode were connected to a SI 1287 Solartron electrical interface, and the catalysts were condition by sweeping from 0 volts to 5 volts at 0.1 V/sec and then back again. The process was repeated 16 times. Then the sensor was exposed to either nitrogen, oxygen, dry air or pure $CO_2$, and the sweeps were recorded. The last sweep is shown in FIG. 16. Notice that there is a sizable peak at an applied voltage of 4 volts in pure $CO_2$. That peak is associated with the electrochemical conversion of $CO_2$.

Notice that the peak is absent when the sensor is exposed to oxygen or nitrogen, but it is clearly seen when the sensor is exposed to air containing less than 400 ppm of $CO_2$. Further the peak grows as the $CO_2$ concentration increases. Thus, the sensor can be used to detect the presence of $CO_2$.

Figure 17:
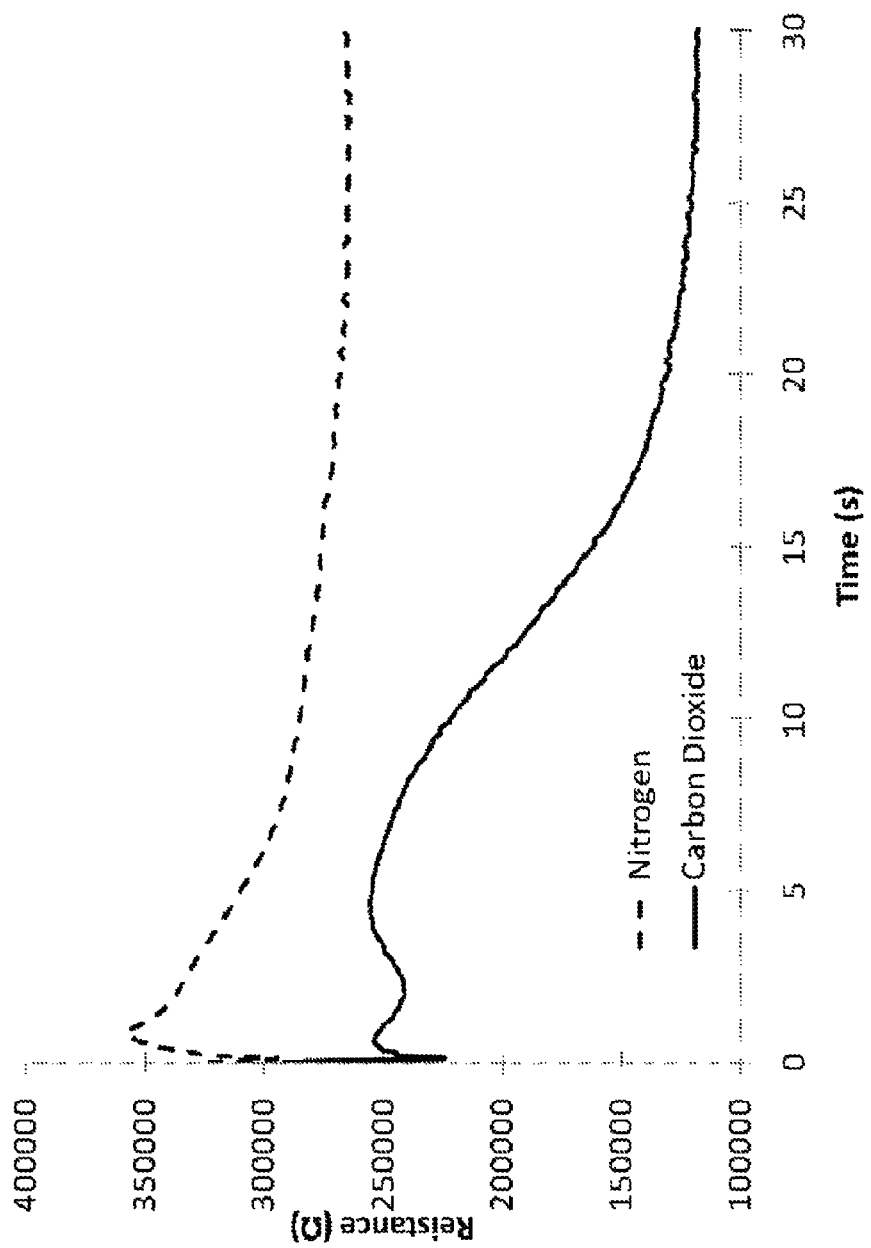
FIG. 17 represents the resistance of the sensor, in nitrogen and in carbon dioxide. The resistance was determined by measuring the voltage needed to maintain a current of 1 microamp. Time is the time from when the current was applied.

We have also run the sensor in a galvanastatic mode, where we measured the voltage needed to maintain the current constant at 1 microamp, and measured the voltage of the device. FIG. 17 shows that less voltage is needed to maintain the current when $CO_2$ is added to the cell. This shows that the sensor that includes an Active Element, Helper Catalyst Mixture responds to the presence of $CO_2$.

Table 4 compares the sensor here to those in the previous literature. Notice that the new sensor uses orders of magnitude less energy than commercial $CO_2$ sensors. This is a key advantage for many applications.

This example also illustrates that the invention can be practiced with a fourth Active Element, gold.

TABLE 4

(Comparison of power needed to run the present sensor to that needed to operate commercially available $CO_2$ sensors)

| Sensor | Power | Sensor | Power |
|---|---|---|---|
| Specific Example 6 | $5 \times 10^{-7}$ watts | GE Ventostat 8100 | 1.75 watts |
| Honeywell C7232 | 3 watts | Vaisala CARBOCAP GMP343 | about 1 watt |

Specific Example 7

Steady State Production of Carbon Monoxide

This experiment used the flow cell described in T. Whipple, E. C. Finke, and P. J. A. Kenis, Electrochem. & Solid-State Lett., 2010, 13 (9), B109-B111 (the Whipple paper). First, catalyst inks were prepared as follows:

For the cathode: 10 mg of silver nanoparticles (Sigma Aldrich) was sonicated into a solution containing 100 µL of water, 100 µL of isopropyl alcohol and 5.6 µL of 5% Nafion® (perfluorosulfonic acid) solution (Ion Power). The resultant catalyst ink was painted on a 1×1.5 cm section of a 2×3 cm piece of carbon paper (Ion Power) and dried with a heat lamp.

The preparation was identical for the anode except 4 mg of HiSpec 1000 platinum black (Sigma Adrich) was substituted for the silver.

Both catalysts were mounted in the flow cell described in the Whipple Paper. Five sccm of $CO_2$ was fed to the anode, and a solution containing 18 mole percent of EMIM-BF4 in water was fed into the gap between the anode and the cathode. At any one time the cell contained approximately 10 mg of silver nanoparticles and approximately 40 mg of EMIM-BF4 Helper Catalyst. A potential was applied to the cell, and the data in Table 5 were obtained. These results demonstrate that steady state production of useful products can be obtained with Catalytically Active Element-Helper Catalyst Mixtures.

TABLE 5

(Products produced at various conditions)

| Cathode potential Volts vs. RHE | Hydrogen production rate, µg/min | Carbon monoxide production rate, µg/min |
|---|---|---|
| −0.358 | 0 | 0 |
| −0.862 | 1.1 | 2.6 |
| −1.098 | 1.4 | 50 |
| −1.434 | 1.1 | 250 |
| −1.788 | 0 | 560 |

Specific Example 8

Demonstration of that Polymers Containing Imidazolium Groups can Act as Helper Catalysts Preparation of a PSMIM, a polymer containing imidazolium groups. "PSMIM" refers to a co-polymer of polystyrene and poly 1-(p-vinylbenzyl)-3-methyl-imidazolium:

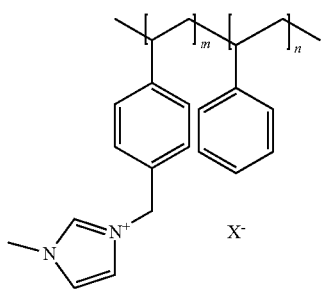

where $X^-$ is an anion, in >0 and n>0.

A copolymer, which is designated here as PSMIM (Cl), was prepared following the synthetic route in U.S. patent application Ser. No. 14/704,935.

The inhibitor-free styrene was prepared by passing styrene (Sigma-Aldrich, Saint Louis, Mo.) through the tert-butylcatechol (TBC) inhibitor remover (Sigma-Aldrich 311340). In general, 40 ml of remover is sufficient to yield 50 ml of clear, inhibitor free styrene Inhibitor TBC in 4-vinylbenzyl chloride (4-VBC) was removed by the same inhibitor remover in a similar fashion.

Poly(4-vinylbenzyl chloride-co-styrene) was then synthesized by heating a solution of inhibitor-free styrene (Sigma-Aldrich) (36.139 g, 350 mmol) and 4-vinylbenzyl chloride (Sigma-Aldrich) (29.7272 g, 190 mmol) in chlorobenzene (Sigma-Aldrich) (45 ml) at 60-65° C. in an oil bath for approximately 20 hours under argon gas with AIBN (α,α'-Azoisobutyronitrile, Sigma-Aldrich) (0.5927 g, 0.90 wt % based on the total monomers' weight) as initiator. The copolymer was precipitated in $CH_3OH$ (methanol) and dried under vacuum.

"Polystyrene methyimidazolium chloride" (PSMIM) was synthesized by adding 1-methylimidazole (Sigma-Aldrich) (2.8650 g, 034.9 mmol), which is an alkylimidazole, to the solution of the poly(4-VBC-co-St) (5.0034 g, 19.4 mmol) in anhydrous N,N-Dimethylformamide (DMF) (Sigma-Aldrich) (30 mL) The mixture was then stirred at around 30° C. for around 50 hours to form a PSMIM solution.

"4-VBC-co-St" or "poly(4-vinylbenzyl chloride co-styrene)" as used here refers to a co-polymer of styrene and 4-vinylbenzyl chloride:

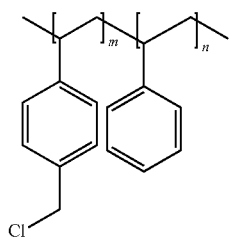

PSMIM-DVB was synthesized starting with poly(4-vinylbenzyl chloride co-styrene.) 1-methylimidazole (Sigma-Aldrich) (3.912 g, 47.7 mmol) was added in a 250 ml 3-neck round bottom flask to the solution of the poly(4-VBC-co-St) (15.358 g, 59.8 mmol) in anhydrous N,N-Dimethylformamide (DMF) (Sigma-Aldrich) (105 mL) 0.22 ml of a divinylbenzene (DVB) in DMF solution (DVB concentration=0.0083 g/ml) was carefully added through a pipette to the mixture with continual magnetic stirring. After this, 0.22 ml of AIBN-DMF solution (AIBN concentration=0.0083 g/ml) was added to the mixture in a similar fashion. The reaction was then kept under nitrogen atmosphere at 50° C. for about 60 hours. PSMIM-DVB was obtained as a white powder after purification by precipitation into diethyl ether.

Membranes were prepared by casting the PSMIM-DVB solution prepared above directly onto a flat glass surface. The thickness of the solution on the glass was controlled by a film applicator (MTI Corporation, Richmond, Calif.) with an adjustable doctor blade. The membranes were then dried in a vacuum oven in the following step wise fashion. They were first kept at 80° C. for 120 minutes, then at 100° C. for 60 minutes, at 120° C. for 30 minutes and finally at 150° C. for 60 minutes. Chloride ions in the membranes were removed by soaking the membranes in 1 M KOH solution for 24 hours or longer.

The cathode layer in Specific Example 8 was prepared as follows. Silver ink was made by mixing 100 mg of silver nanoparticles (20-40 nm, 45509, Alfa Aesar, Ward Hill, Mass.), 5 mg porous carbon (Vulcan XC-72R, Fuel Cell Earth, Woburn, Mass.) and different amounts of PSMIM-Cl in 3 ml of ethanol (459844, Sigma-Aldrich, St. Louis, Mo.). The mixture was then sonicated for 10 minutes. The silver ink was painted onto a gas diffusion layer (Sigracet 35 BC GDL, Ion Power Inc., New Castle, Del.) covering an area of 6 cm×6 cm. The electrode was immersed in 1 M KOH for at least 1 hour so that PSMIM-Cl converted by ion exchange to PSMIM-OH. Then the electrode was cut into 2.5 cm×2.5 cm sections for cell testing.

The anode in Specific Example 8 was prepared as follows: 100 mg of $IrO_2$ (43396, Alfa Aesar, Ward Hill, Mass.) was dispersed in the mixture of 1 ml of deionized water, 2 ml of isopropanol (3032-16, Macron Fine Chemicals, Avantor Performance Materials, Center Valley, Pa.) and 0.1 ml of 5 wt. % poly-tetrafluoroethylene (PTFE) dispersion (665800, Sigma-Aldrich, St. Louis, Mo.). The mixture was sonicated for 10 min using a water bath sonicator. The ink was painted onto 6 cm×6 cm of carbon fiber paper (Toray Paper 120, Fuel Cell Earth, Woburn, Mass.). The actual $IrO_2$ loading was about 2 mg/cm². The electrode was cut into 3 cm×3 cm sections for cell testing.

The membrane was sandwiched between the anode and the cathode with the metal-containing layers on the anode and cathode facing the membrane, and the whole assembly was mounted in a Fuel Cell Technologies 5 cm² fuel cell hardware assembly with serpentine flow fields.

$CO_2$ humidified at 25° C. was fed into the cathode flow field at a rate of 20 sccm, and 10 mM $KHCO_3$ was fed into the anode flow field. The cyclic voltammograms were collected by scanning the cell potential from 1.2 to 3.0 V. All of the scans were made at room temperature and atmospheric pressure.

Figure 18:
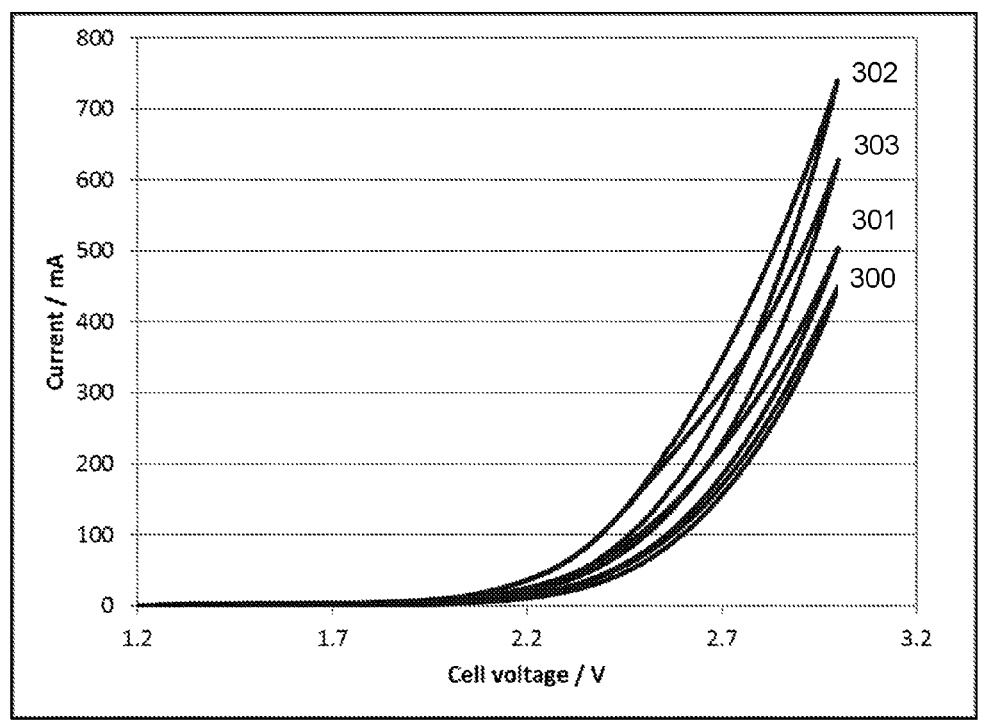
FIG. 18 shows how the voltammograms of a 5 $cm^2$ cell change when 0% (200), 1% (201), 5% (202), and 10% (203) of PSMIMCl are added to the $CO_2$ electrolyzer cathode catalyst layer, where the percentage is calculated as the weight of the PSMIMCl divided by the weight of the silver.

FIG. 18 shows the results. Plot 300 is a base case with no PSMIM in the cathode catalyst layer ink. Notice that the current increases when PSMIM is added to the catalyst layer in a later sample, such that the PSMIM weight is 1% of the weight of the silver (plot 301). Further increases in the current are seen as the PSMIM concentration is increased so that the PSMIM weight is 5% of the weight of the silver (plot 302). Then there is a small decrease when the weight of the PSMIM is increased to 10% of the weight of the silver (plot 303). A decrease in the selectivity of the reaction was observed.

Notice that $CO_2$ conversion starts to occur at a cell voltage of about 1.7 V in the presence of the PSMIM membrane. This corresponds to an overpotential of about 0.4 V, compared to over 1 volt in table 2. Clearly, PSMIM is acting as a helper catalyst.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

While particular elements, embodiments and applications of the present invention have been shown and described, it will be understood, that the invention is not limited thereto, since modifications can be made by those skilled in the art without departing from the scope of the present disclosure, particularly in light of the foregoing teachings.

What is claimed is:

1. An electrochemical device comprising:
   an anode and a cathode, the cathode comprising at least one Catalytically Active Element, the at least one Catalytically Active Element contacting both a Positively Charged Cyclic Amine and carbon dioxide ($CO_2$), wherein said Positively Charged Cyclic Amine comprises a polymer and wherein, when electrical energy is applied to create a cell voltage between the anode and the cathode, the electrochemical device is capable of converting at least a portion of the $CO_2$ to a carbonaceous product when the cell voltage is equal to 2.8 V, the conversion effectuated electrochemically with electrical energy as the primary energy source, said carbonaceous product consisting of one of CO, $HCO^-$, $H_2CO$, $(HCOO)^-$, HCOOH, $CH_4$, $C_2H_4$, $CH_3CH_2OH$, $CH_3OH$, $CH_3COO^-$, $CH_3COOH$, $C_2H_6$, $(COOH)_2$ and $(COO^-)_2$.

2. The electrochemical device of claim 1 wherein said Positively Charged Cyclic Amine comprises a five-member or a six-member aromatic ring, wherein all ring nitrogen atoms are attached only to non-hydrogen atoms.

3. The electrochemical device of claim 1, wherein the predominant carbonaceous product consists of one of carbon monoxide (CO), formic acid (HCOOH) or formate ions $(HCOO^-)$.

4. The electrochemical device of claim 1, wherein the predominant carbonaceous product is one of formic acid (HCOOH) or formate ions $(HCOO)^-$), and wherein the Positively Charged Cyclic Amine comprises an imidazolium or a pyridinium.

5. The electrochemical device of claim 1, wherein the Catalytically Active Element is selected from the group consisting of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, C, In, Tl, Pb, Bi, Sb, Te, U, Sm, Tb, La, Ce and Nd.

6. The electrochemical device of claim 5, wherein the Catalytically Active Element comprises at least one of Ag, Au, Zn, Cd, Pd, Ga and Ni.

7. The electrochemical device of claim 5, wherein the Positively Charged Cyclic Amine comprises an imidazolium or a pyridinium.

8. The electrochemical device of claim 1, wherein the cathode has a cathode potential, and wherein the predominant carbonaceous product is carbon monoxide (CO) and at least a portion of the $CO_2$ is convertible to CO when the cathode potential is equal to or less negative than −0.75 V versus the Standard Hydrogen Electrode (SHE).

9. The electrochemical device of claim 1, wherein the cathode has a cathode potential, and wherein the electrochemical device is capable of converting at least a portion of the $CO_2$ to the predominant carbonaceous product when the cathode potential is equal to or less negative than −0.75 V versus the Standard Hydrogen Electrode (SHE).

10. The electrochemical device of claim 1, wherein the cathode has a cathode potential, and wherein at least a portion of the $CO_2$ is convertible to the predominant carbonaceous product when the cathode potential is equal to or less negative than −0.6 V versus the Standard Hydrogen Electrode (SHE).

11. The electrochemical device of claim 1, wherein the cathode has a cathode potential, and wherein at least a portion of the $CO_2$ is convertible to the predominant carbonaceous product when the cathode potential is equal to or less negative than −0.4 V versus the Standard Hydrogen Electrode (SHE).

12. The electrochemical device of claim 1 comprising a $CO_2$ sensor or a fuel cell.

13. The electrochemical device of claim 12, wherein the device is a $CO_2$ sensor and the Catalytically Active Element is Au.

14. The electrochemical device of claim 12 wherein the device shows a response to $CO_2$ when there is a potential difference of from 2.7 to 4.3 volts between the anode and cathode.

15. The electrochemical device of claim 13, wherein the Positively Charged Cyclic Amine comprises an imidazolium.

16. The electrochemical device of claim 1 wherein the Positively Charged Cyclic Amine is a Helper Catalyst, wherein said Positively Charged Cyclic Amine comprises a polymer and wherein a substance S is identifiable as a Helper Catalyst for an electrochemical reaction R that is catalyzed by a Catalytically Active Element M by applying a test comprising:
   filling a three-electrode electrochemical cell with an electrolyte E suitable for effectuating reaction R, said electrochemical cell comprising a working electrode, a counter electrode and a reference electrode;
   electrically connecting said Catalytically Active Element M to said working electrode and electrically connecting said working electrode to said counter electrode and to a source of electrical energy, thereby forming an electrical circuit;
   employing said reference electrode to measure a reversible hydrogen electrode (RHE) potential in said electrolyte E;

loading at least one reactant for reaction R into said cell;

measuring a cyclic voltammogram for reaction R to identify a potential of a peak associated with reaction R;

calculating a difference V1 between RHE and an onset potential of said peak associated with reaction R;

calculating a difference V1A between RHE and a maximum potential of said peak associated with reaction R;

adding to said electrolyte E between 0.0001% and 99.9999% by weight of said Helper Catalyst;

measuring an RHE potential in electrolyte E with said added Helper Catalyst;

measuring a cyclic voltammogram of reaction R with said added Helper Catalyst;

calculating a difference V2 between RHE and an onset potential of said peak associated with reaction R;

calculating a difference V2A between RHE and a maximum potential of said peak associated with reaction R;

determining whether V2<V1 or V2A<V1A at any concentration of said Helper Catalyst between 0.0001% and 99.9999%; and identifying substance S as said Helper Catalyst for reaction R at concentrations at which V2<V1 or V2A<V1A.

* * * * *